United States Patent [19]

Flynn et al.

[11] Patent Number: 5,109,010
[45] Date of Patent: Apr. 28, 1992

[54] DIBENZOFURANYL SUBSTITUTED 1,5-DIHYDRO-4-(N-METHYLHYDROX-YLAMINO)-2H-PYRROL-2-ONES

[75] Inventors: Gary A. Flynn; Douglas W. Beight, both of Cincinnati, Ohio

[73] Assignee: Merrell Dow Pharmaceuticals Inc., Cincinnati, Ohio

[21] Appl. No.: 680,959

[22] Filed: Apr. 5, 1991

Related U.S. Application Data

[62] Division of Ser. No. 380,937, Jul. 17, 1989, Pat. No. 5,026,861.

[51] Int. Cl.$^5$ .................... A61K 31/44; A61K 31/40; C07D 207/273

[52] U.S. Cl. .................... 514/337; 514/422; 514/825; 514/826; 546/269; 548/518; 548/525

[58] Field of Search ............... 514/337, 422, 825, 826; 548/518, 525; 546/269

[56] References Cited

U.S. PATENT DOCUMENTS 5,026,861 6/1991 Flynn .................... 514/424

Primary Examiner—C. Warren Ivy
Assistant Examiner—Amelia A. Owens
Attorney, Agent, or Firm—William J. Stein

[57] ABSTRACT

Novel cyclic vinylogous N-hydroxy-N-methylureas are useful in the treatment of leukotriene mediated conditions such as asthma and rheumatoid arthritis.

9 Claims, No Drawings

DIBENZOFURANYL SUBSTITUTED 1,5-DIHYDRO-4-(N-METHYLHYDROX-YLAMINO)-2H-PYRROL-2-ONES

This is a divisional of application Ser. No. 07/380,937, filed Jul. 17, 1989 now U.S. Pat. No. 5,026,861.

Research in the area of allergic reactions has provided evidence that arachidonic acid derivatives formed by the action of lipoxygenases and generally refered to as leukotrienes are related to various disease states. This invention relates to novel chemical agents which are selective lipoxygenase inhibitors useful in the treatment of conditions such as asthma and rheumatoid arthritis where leukotrienes are thought to be causal mediators.

The chemical agents of this invention are compounds of the formula:

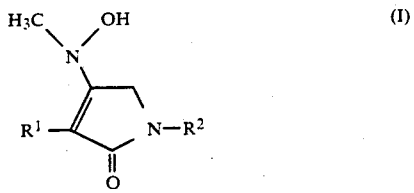

wherein $R^1$ is selected from the group consisting of naphthyl, dibenzofuranyl, and phenyl, where the phenyl group is optionally substituted with methoxy, chloro, trifloromethyl, phenyl, phenoxy, or benzyloxy, and $R^2$ is selected from the group consisting of methyl, pyridyl and phenyl where the phenyl group is optionally substituted with methylthio and methylsulfinyl.

The optional substituents on the $R^1$ and $R^2$ groups are located at the 4- or para position of the phenyl ring. The $R^2$ pyridyl group is attached to the pyrrol nitrogen at its 4 or 3 carbon.

The compounds of this invention are prepared by a procedure set forth in the following reaction schemes.

REACTION SCHEME A

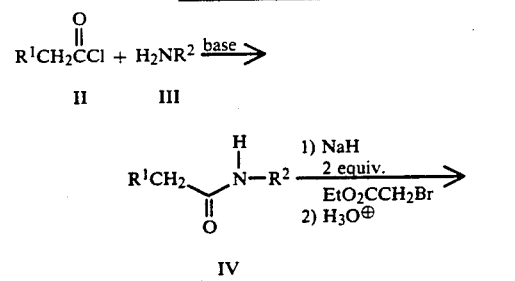

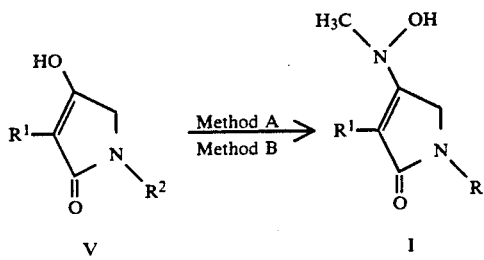

REACTION SCHEME B

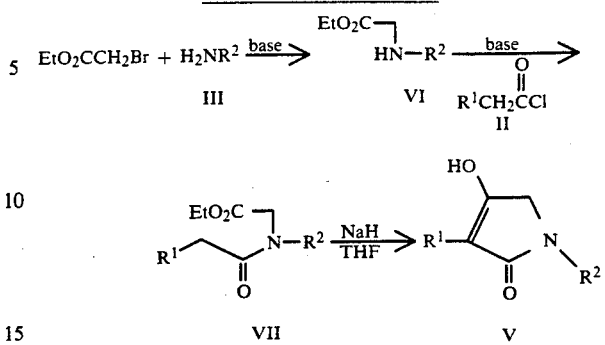

Generally the compounds of formula I are produced (Method A) by reacting triethylamine (Et$_3$N) with a 4-hydroxy-(2H)-pyrrole-2-one of formula V and N-methylhydroxylamine hydrochloride in dimethylsulfoxide (DMSO), under argon atmosphere and at about 90° C. An alternate method (B) utilizes sodium acetate and acetic acid instead of Et$_3$N in the above method A which generally results in increased yields under less basic conditions.

Reaction Scheme A shows that the appropriate 4-hydroxy-(2H)-pyrrole-2-one of formula V can be produced by reacting the appropriate aryl amine (III) with an appropriate arylacetyl chloride (II) in the presence of a base to produce the acetamide compound IV which then is first deprotonated with sodium hydride and next alkylated with ethyl bromoacetate (EtO$_2$CCH$_2$Br). Alkylation of IV may be accompanied by in situ cyclization when excess base is used. The resulting solution is then carefully added to water and acidified to produce the cyclized compound of formula V.

Alternatively, Reaction Scheme B shows that an appropriate aryl amine (III) is reacted with ethyl bromoacetate (EtO$_2$CCH$_2$Br) in the presence of a base such as sodium hydride to produce the glycinate compounds of formula VI, which are further reacted with an appropriate arylacetyl chloride (II) in a base such as pyridine, resulting in a glycinate compound of formula VII, which is finally cyclized in a Dieckman reaction using sodium hydride as the base in tetrahydrofuran to produce the appropriate 4-hydroxy-(2H)-pyrrole-2-one of formula V. The starting materials for either Reaction Scheme A or B are readily commercially available or the synthetic route to make the material is disclosed below.

The following specific examples are presented to illustrate the synthesis of the compounds of this invention, but they should not be construed as limiting the scope of this invention in any way.

EXAMPLE 1

N-Phenyl 2-Phenylacetamide (IVa)

To a stirred solution of 9.3 g (0.10 Mole) of aniline (IIIa) and 8.3 g (0.10 Mole) pyridine in 100 mL CH$_2$Cl$_2$ at 0° C. under an argon atmosphere was added a solution of 15.5 g (0.10 Mole) phenylacetyl chloride (IIa) in 25 mL CH$_2$Cl$_2$ over a 30 minute period. The solution was allowed to warm to 25° C. over 1 hour and was quenched into 200 mL H$_2$O. The aqueous layer was washed with two 100 mL portions of CH$_2$Cl$_2$ and the combined organic layers were washed with two 100 mL portions of 10% HCl solution. The organic extract was dried over MgSO₄, filtered, concentrated, and crystallized from CH₂Cl₂/hexane to give 20.07 g (95%) of colorless needles. mp. 115°–116° C. δ¹H-NMR (CDCl₃) ppm 7.0–7.6 (m, 11H); 3.67 (S, 2H).

By substituting the starting materials indicated below for IIa and IIIa and following the procedure set forth in Example 1 above, the following compounds can be produced:

2-(4-benzyloxyphenyl)-N-phenylacetamide (IVb)

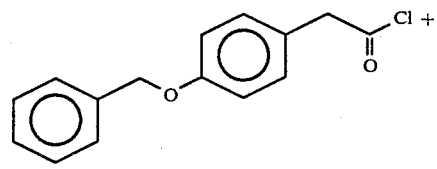

IIb

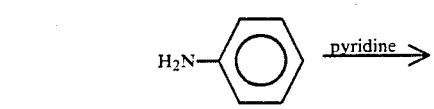

IIIa

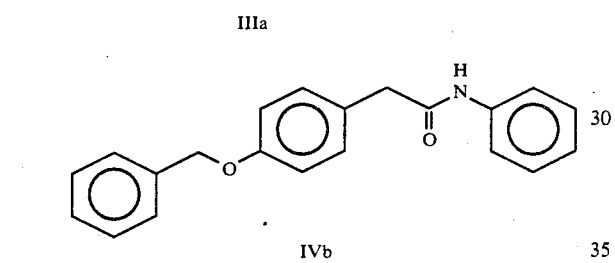

IVb 2-(4-benzyloxyphenyl)-N-methylacetamide (IVc)

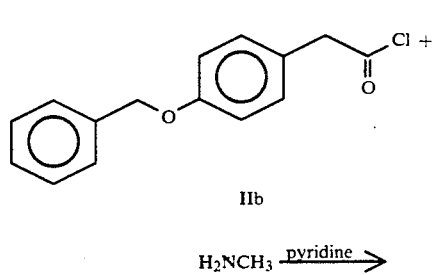

IIb

H₂NCH₃ —pyridine→

IIIb

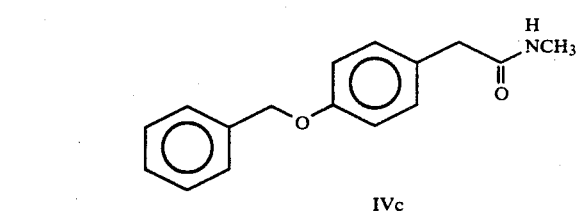

IVc 2-(4-methoxyphenyl)-N-phenylacetamide (IVd)

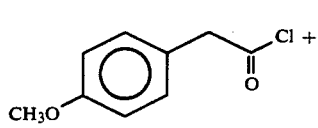

IIc

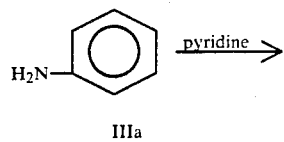

IIIa

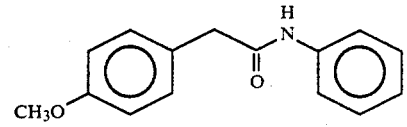

IVd 2-(4-phenoxyphenyl)-N-phenylacetamide (IVe)

IId

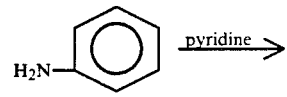

IIIa

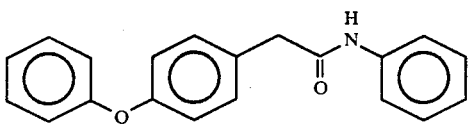

IVe 2-(2-dibenzofuranyl)-N-phenylacetamide (IVf)

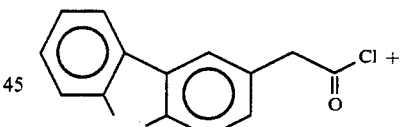

IIe

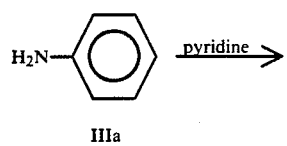

IIIa

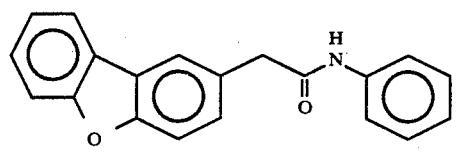

IVf 2-(4-chlorophenyl)-N-phenylacetamide (IVg)

-continued
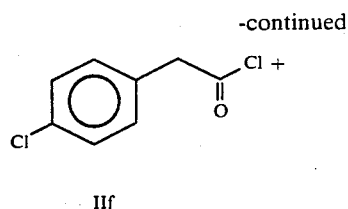
IIf
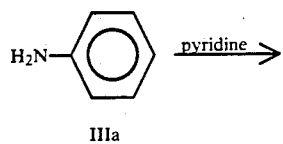
IIIa
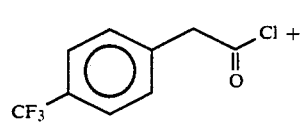
IVg
N-phenyl-2-(4-trifluoromethyl)acetamide (IVh)
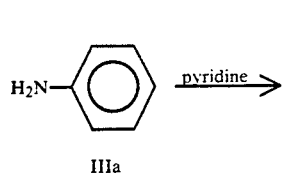
IIg
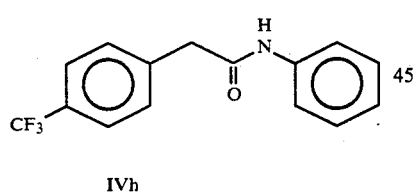
IIIa
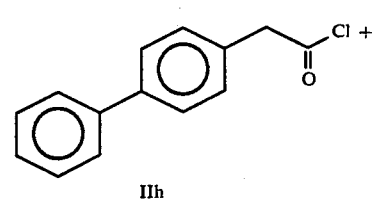
IVh
2-(4-biphenyl)-N-phenylacetamide (IVi)
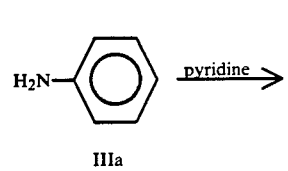
IIh
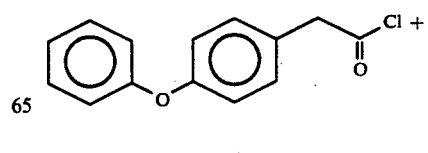
IIIa
-continued
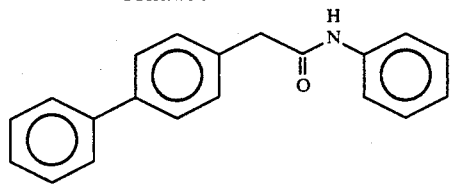
IVi
2-(2-naphthyl)-N-phenylacetamide (IVj)
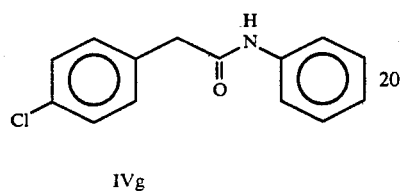
IIi
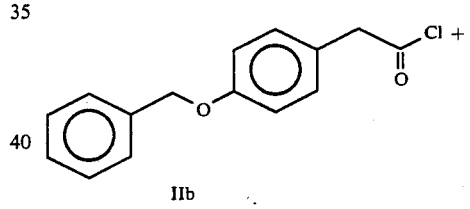
IIIa
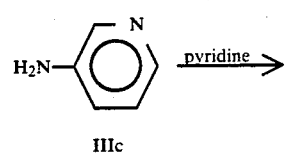
IVj
2-(4-benzyloxyphenyl)-N-(3-pyridyl)acetamide (IVk)
IIb
IIIc
IVk
2-(4-phenoxyphenyl)-N-(3-pyridyl)acetamide (IVl)
IId -continued
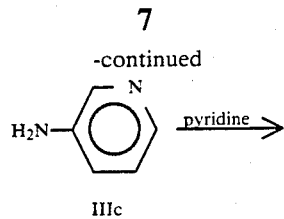
IIIc
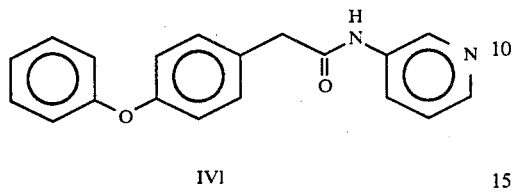
IVl
2-(2-dibenzofuranyl)-N-(3-pyridyl)acetamide (IVm)
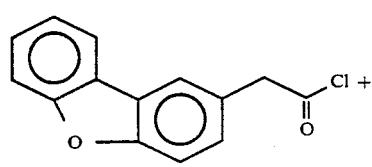
IIe
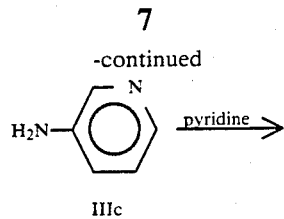
IIIc
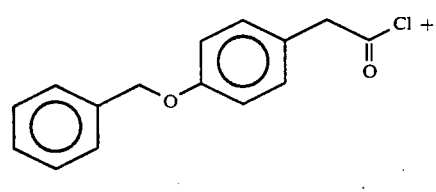
IVm
2-(4-benzyloxyphenyl)-N-(4-pyridyl)acetamide (IVn)
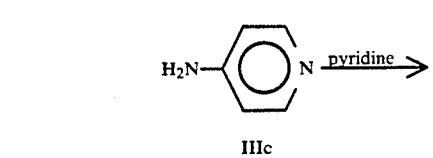
IIb
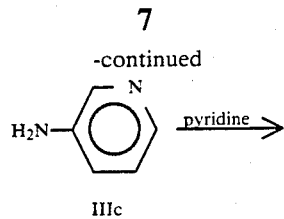
IIIc
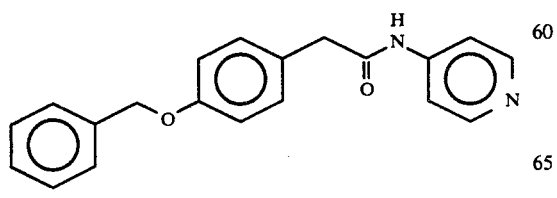
IVn
2-(4-phenoxyphenyl)-N-(4-pyridyl)acetamide (IVo)
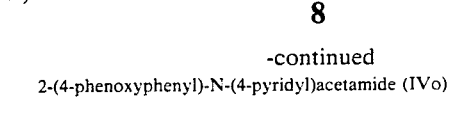
IId
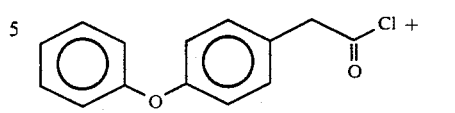
IIId
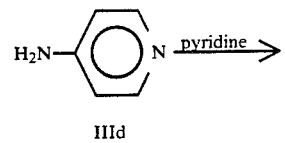
IVo
2-(2-dibenzofuranyl)-N-(pyridyl)acetamide (IVp)
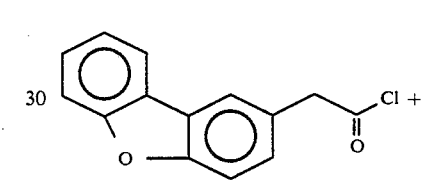
IIe
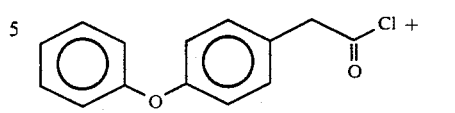
IIId
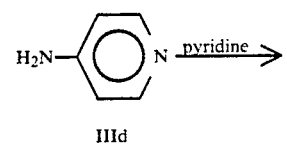
IVp
2-(4-benzyloxyphenyl)-N-(4-methylthiophenyl)acetamide (IVq)
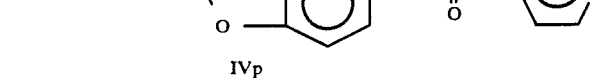
IIb
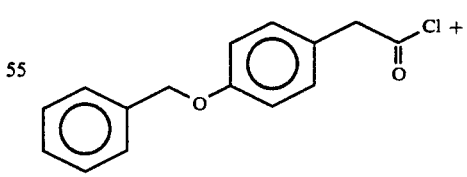
IIIe

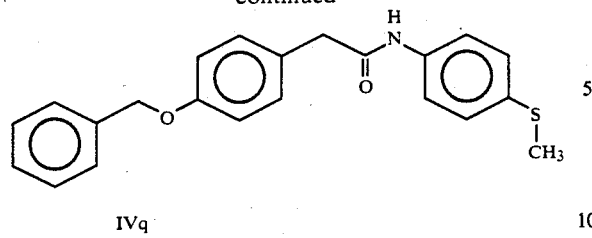

IVq

N-(4-methylthiophenyl)-2-(4-phenoxyphenyl)acetamide (IVr)

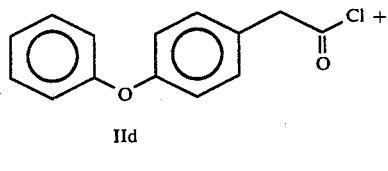

IId

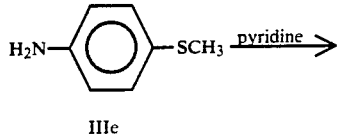

IIIe

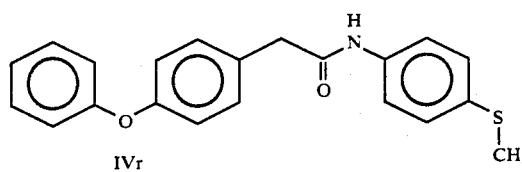

IVr 2-(2-dibenzofuranyl)-N-(4-methylthiophenyl)-acetamide (IVs)

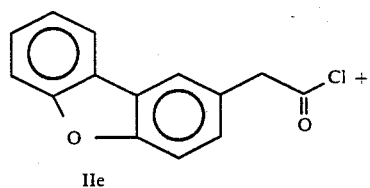

IIe

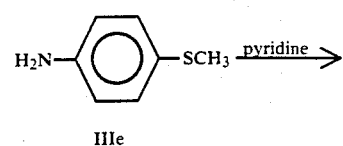

IIIe

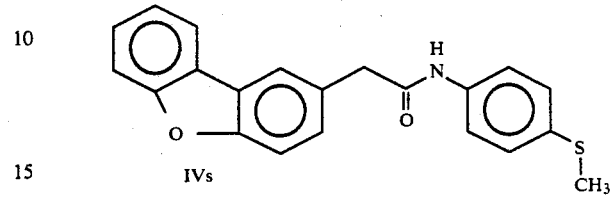

IVs

EXAMPLE 2

1,5-dihydro-1,3-diphenyl-4-hydroxy-2H-pyrrol-2-one (Va)

To a stirred slurry of 500 mg (12 mmol) of a 60% oil dispersion of sodium hydride (which had been washed with hexane) in 12 ml dry DMF under argon atmosphere was added 1.06 g (5.0 mmol) of N-phenyl-2-phenyl acetamide (IVa) in 5 mL dry DMF. Gas evolution had ceased after 30 minutes and 0.560 mL (5.0 mmol) of ethyl bromoacetate was added via syringe. The solution was stirred at 25° C. for 30 minutes, then warmed to 80° C. for 4 hours. The cooled solution was carefully poured into 200 mL H$_2$O, washed with ether, filtered over celite and acidified to pH=2. The white precipitate was filtered, washed well with H$_2$O and dried under high vacuum to give 1.04 g (4.0 mmol, 80% yield) of 1,3-diphenyl-2,4-pyrrolidinedione Ia, mp 285°–287° C.

(Dec.): IR(KBr) 3500–2400 (b, OH), 1620, 1400 cm$^{-1}$; $^1$H-NMR (DMSO) ppm δ7.99 (d, 2H, J=6 Hz), 7.73 (d, 2H, J=6 Hz), 7.37 (t, 4H, J=6 Hz), 7.19 (t, 1H, J=6 Hz), 7.05 (t, 1H, J=6 Hz), 4.48 (s, 2H).

By substituting the starting material indicated below, for IVa and following the procedure set forth in Example 2 above, the following compounds V can be produced:

3-(4-benzyloxyphenyl)-1,5-dihydro-4-hydroxy-1-phenyl-2H-pyrrol-2-one (Vb)

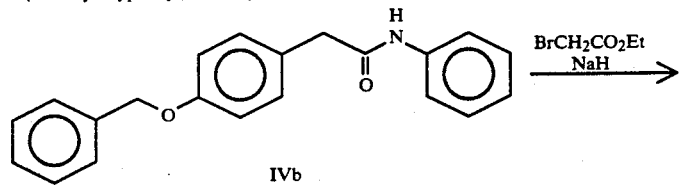

IVb

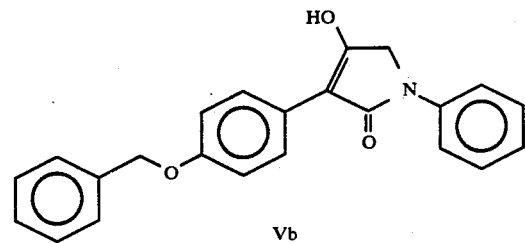

Vb 3-(4-benzyloxyphenyl)-1,5-dihydro-4-hydroxy-1-methyl-2H-pyrrol-2-one (Vc)

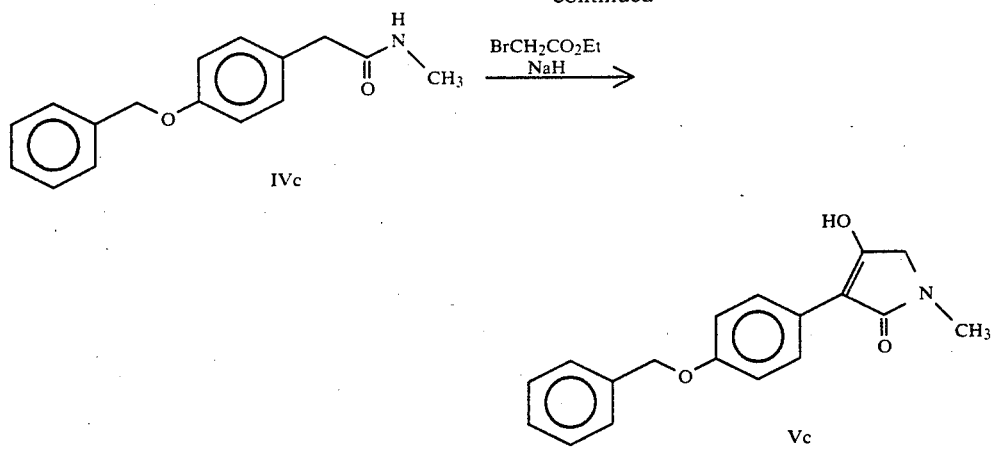
1,5-dihydro-4-hydroxy-3-(4-methoxyphenyl)-1-phenyl-2H-pyrrol-2-one (Vd)
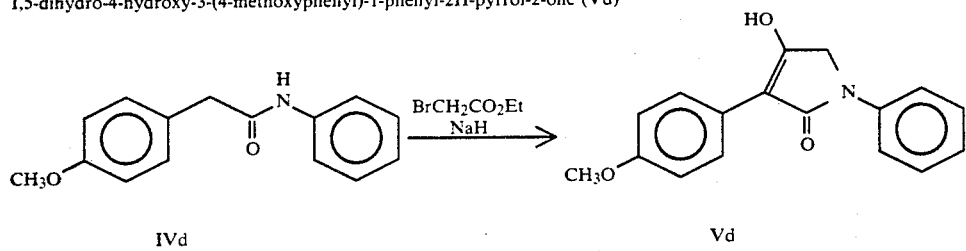
1,5-dihydro-4-hydroxy-3-(4-phenoxyphenyl)-1-phenyl-2H-pyrrol-2-one (Ve)
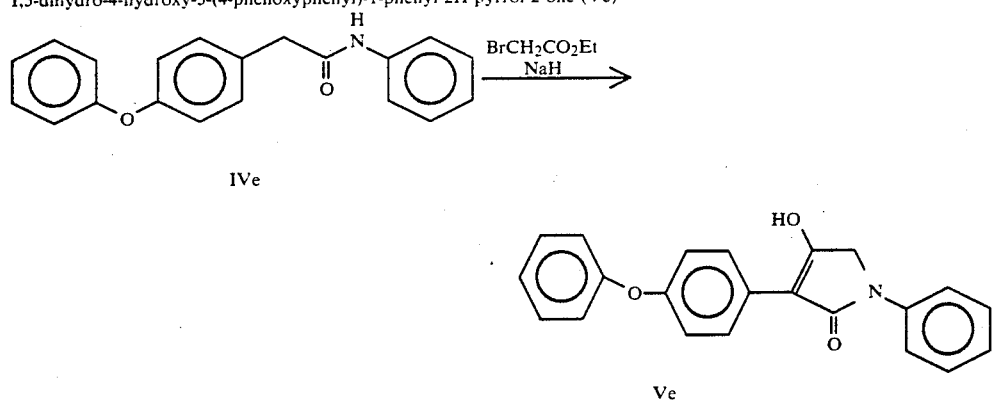
3-(2-dibenzylfuranyl)-1,5-dihydro-4-hydroxy-1-phenyl-2H-pyrrol-2-one (Vf)
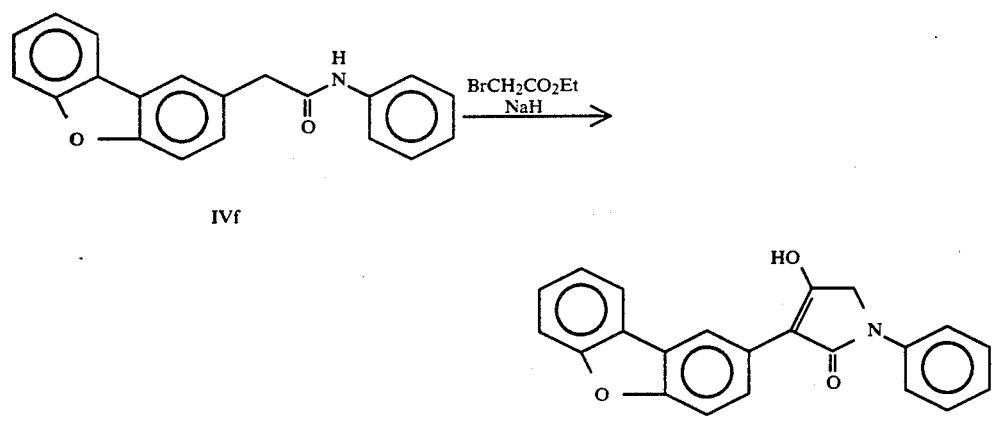
3-(4-chlorophenyl)-1,5-dihydro-4-hydroxy-1-phenyl-2H-pyrrol-2-one (Vg)

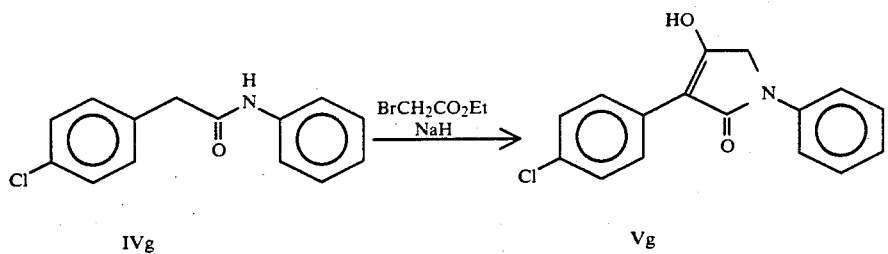
1,5-dihydro-4-hydroxy-1-phenyl-3-(4-trifluoro-methylphenyl)-2H-pyrrol-2-one (Vh)
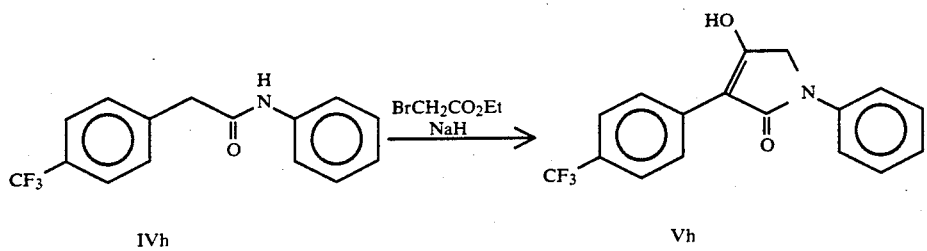
3-(4-biphenyl)-1,5-dihydro-4-hydroxy-1-phenyl-2H-pyrrol-2-one (Vi)
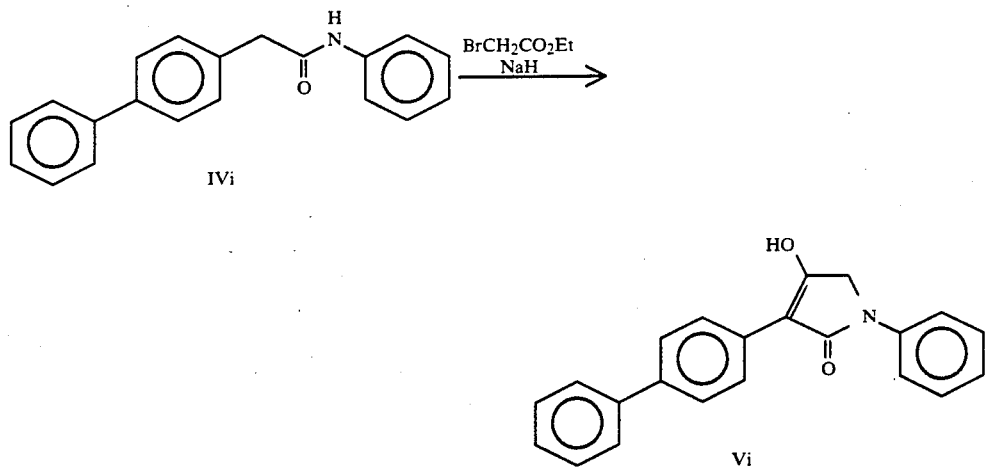
1,5-dihydro-4-hydroxy-3-(2-naphthyl)-1-phenyl-2H-pyrrol-2-one (Vj)
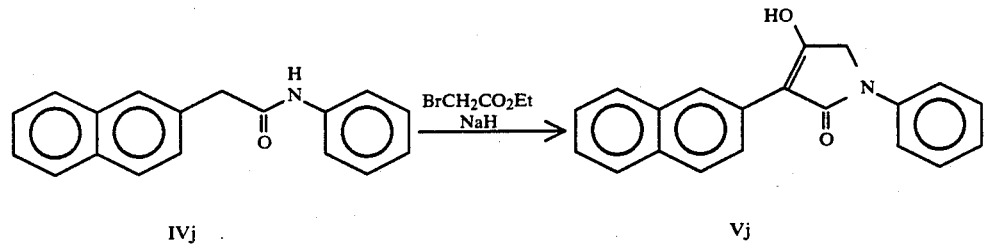
3-(4-benzyloxyphenyl)-1,5-dihydro-4-hydroxy-1-(3-pyridyl)-2H-pyrrol-2-one (Vk)
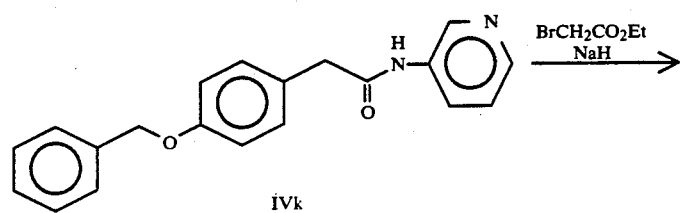

-continued
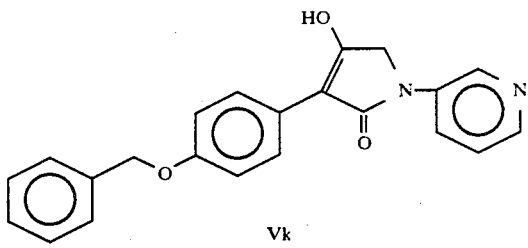
Vk
1,5-dihydro-4-hydroxy-3-(4-phenoxyphenyl)-1-(3-pyridyl)-2H-pyrrol-2-one (Vl)
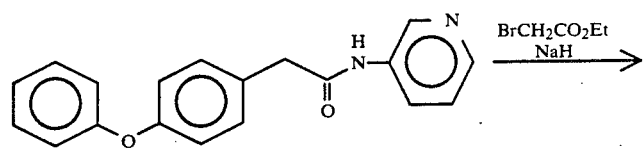
IVl
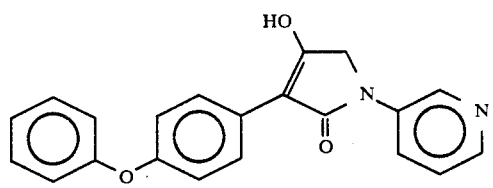
Vl
3-(2-dibenzofuranyl)-1,5-dihydro-4-hydroxy-1-(3-pyridyl)-2H-pyrrol-2-one (Vm)
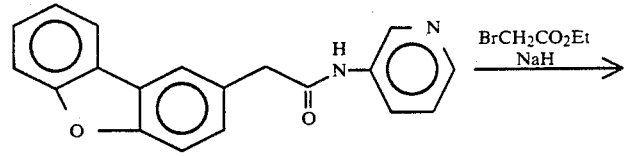
IVm
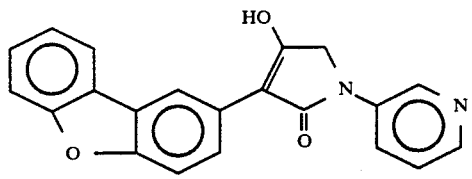
Vm
3-(4-benzyloxyphenyl)-1,5-dihydro-4-hydroxy-1-(4-pyridyl)-2H-pyrrol-2-one (Vn)
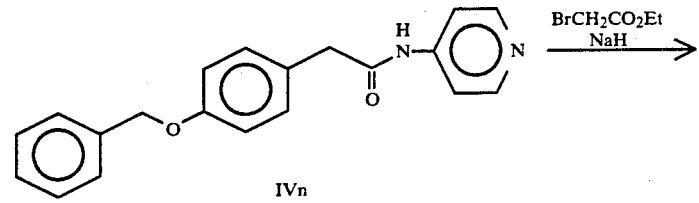
IVn -continued
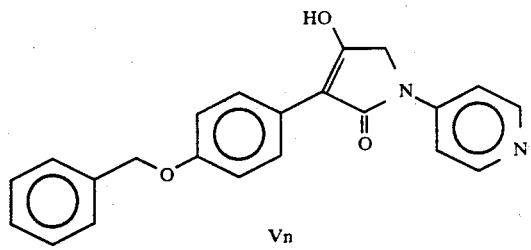
1,5-dihydro-4-hydroxy-3-(4-phenoxyphenyl)-1-(4-pyridyl)-2H-pyrrol-2-one (Vo)
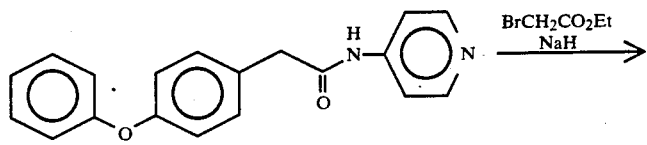
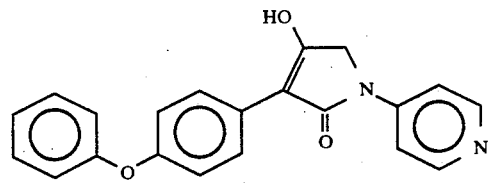
3-(2-dibenzofuranyl)-1,5-dihydro-4-hydroxy-1-(4-pyridyl)-2H-pyrrol-2-one (Vp)
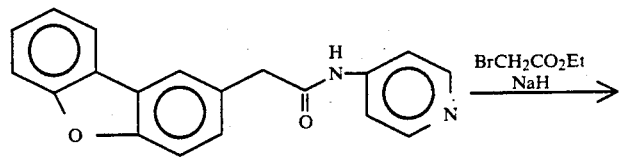
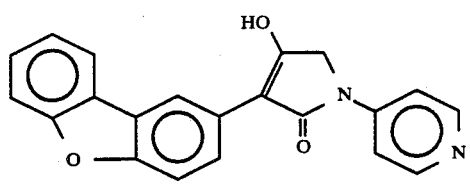
3-(4-benzyloxyphenyl)-1,5-dihydro-4-hydroxy-1-(4-methylthiophenyl)-2H-pyrrol-2-one (Vq)
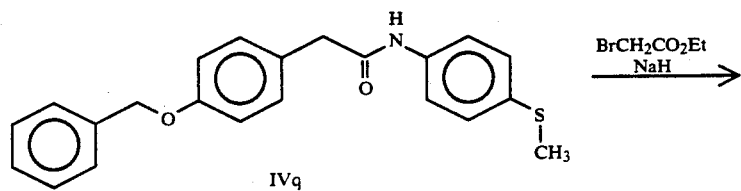

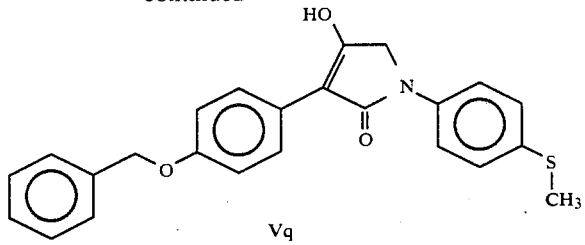

Vq 1,5-dihydro-4-hydroxy-1-(4-methylthiophenyl)-3-(4-phenoxyphenyl)-2H-pyrrol-2-one (Vr)

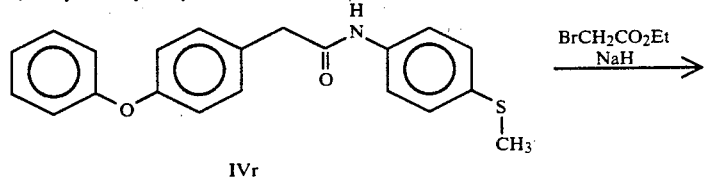

IVr

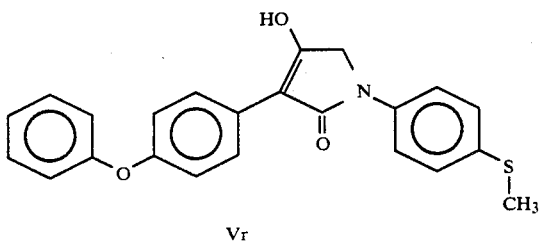

Vr 3-(2-dibenzofuranyl)-1,5-dihydro-4-hydroxy-1-(4-methylthiophenyl)-2H-pyrrol-2-one (Vs)

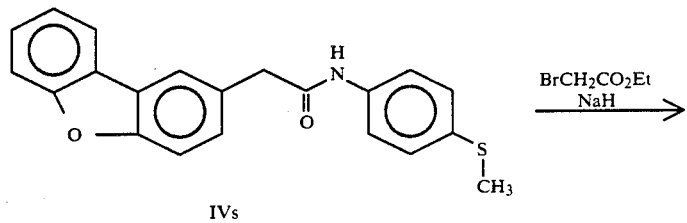

IVs

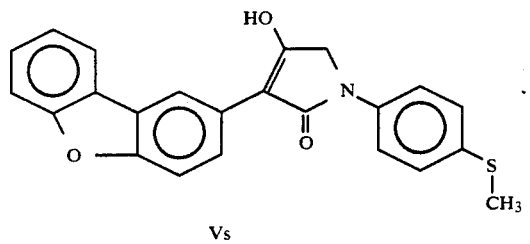

Vs

EXAMPLE 3

1,5-dihydro-1,3-diphenyl-4-(N-methylhydroxylamino)-2H-pyrrol-2-one (Ia)

Method A

To a stirred mixture of 10.0 g (40 mmol) of 1,3-diphenyl-2,4-pyrrolidinedione (Va) and 13.2 g (160 mmol) of N-methylhydroxylamine hydrochloride in 60 mL dry DMSO under argon atmosphere was added 28 mL (200 mmol) of triethylamine. The mixture was heated at 90° C. for 2.5 hours, allowed to cool and stirred at 25° C. for 18 hours. The reaction was poured into 500 mL $H_2O$ and extracted with 350 mL ethyl acetate. The organic extract was washed well with $H_2O$ and brine, dried over $MgSO_4$ and concentrated to give a solid. Trituration with ether and filteration gave 1.13 g of light tan crystals (4.0 mmol, 10% yield), mp 176°–177° C. (dec); IR (KBr) 3426, 3058, 2948, 1607, 1586, 1501, 1380, cm$^{-1}$; $^1$H-NMR (DMSO) ppm δ9.94 (s, 1H), 7.75 (d, 2H, J=6 Hz), 7.35 (m, 6H), 7.25 (m, 1H), 7.05 (t, 1H, J=6 Hz), 4.37 (s, 2H), 2.97 (s, 3H).

Calcd. for $C_{17}H_{16}N_2O_2$: % C=72.84, % H=5.75, % N=9.99. Found: % C=72.83, % H=5.85, % N=9.85.

The combined aqueous layers were filtered, acidified to pH=2 with conc. HCl and the resulting precipitate was filtered, wahsed with water and vacuum dried to give: 9.03 g (36 mmol) of recovered starting material.

Method B

To a stirred mixture of 10.0 g (40 mmol) of 1,3-diphenyl-2,4-pyrrolididedione (Va) and 13.2 g (160 mmol) of N-methylhydroxylamine hydrochloride in 60 mL dry DMSO under argon atmosphere was added 3.3 g (10 mmol) sodium acetate and 6.0 g (100 mmol) of acetic acid. The mixture was heated at 90° C. for 3 hours and allowed to cool. The reaction was poured into 500 mL H₂O and extracted with 350 mL ethyl acetate. The organic extract was washed well with H₂O, filtered, dried over MgSO₄ and concentrated to give a solid. Trituration with ether and filtration gave 4.5 g of light tan crystals (16.0 mmol, 40% yield).

By substituting the indicated material for Va and following the procedure set forth in Example 3 above, the following compounds I can be produced:

3,(4-benzyloxyphenyl)-1,5-dihydro-4-(N-methylhydroxyl-amino)-1-phenyl-2H-pyrrol-2-one (Ib)

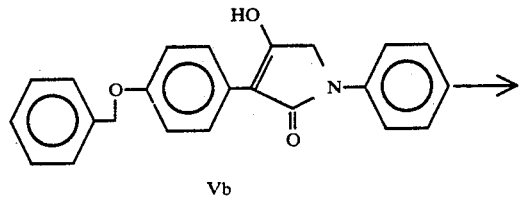

Vb

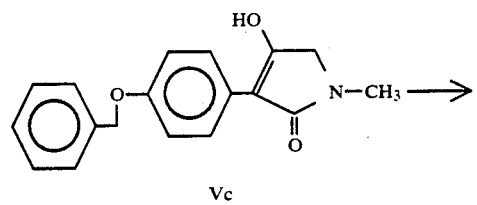

Ib 3-(4-benzyloxyphenyl)-1,5-dihydro-1-methyl-4-(N-methyl-hydroxylamino)-2H-pyrrol-2-one (Ic)

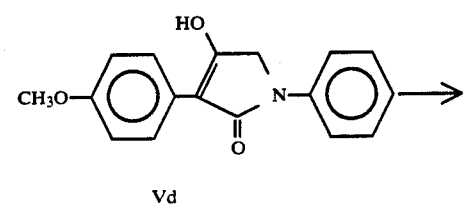

Vc

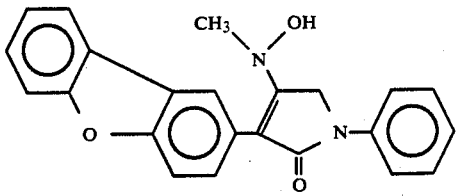

Ic 1,5-dihydro-3-(4-methoxyphenyl)-4-(N-methylhydroxylamino)-1-phenyl-2H-pyrrol-2-one (Id)

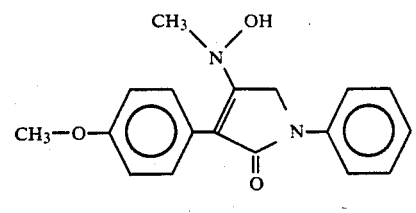

Vd

—continued

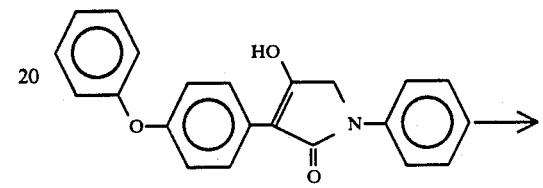

Id 1,5-dihydro-4-(N-methylhydroxylamino)-3-(4-phenoxyphenyl)-1-phenyl-2H-pyrrol-2-one (Ie)

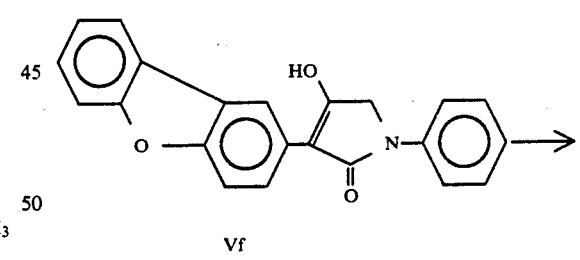

Ve

Ie 3-(2-dibenzofuranyl)-1,5-dihydro-4-(N-methylhydroxylamino)-1-phenyl-2H-pyrrol-2-one (If)

Vf

If 3-(4-chlorophenyl)-1,5-dihydro-4-(N-methylhydroxylamino)-1-phenyl-2H-pyrrol-2-one (Ig)

-continued

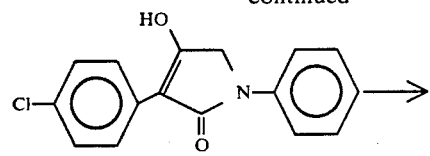
Vg

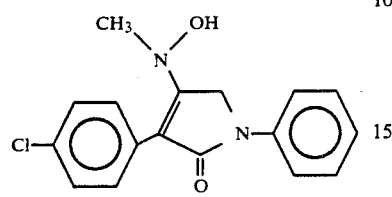
Ig 1,5-dihydro-4-(N-methylhydroxylamino)-1-phenyl-3-(4-trifluoromethylphenyl)-2H-pyrrol-2-one (Ih)

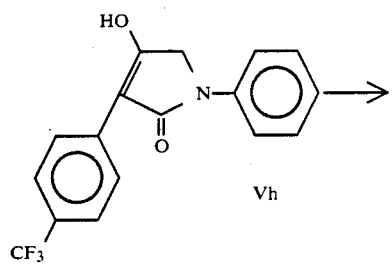
Vh

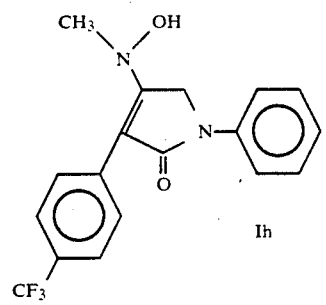
Ih 3-(4-biphenyl)-1,5-dihydro-4-(N-methylhydroxylamino)-1-phenyl-2H-pyrrol-2-one (Ii)

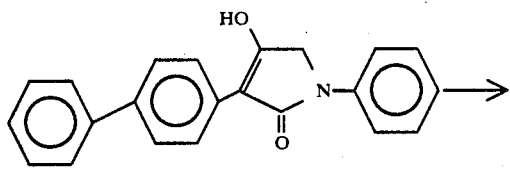
Vi

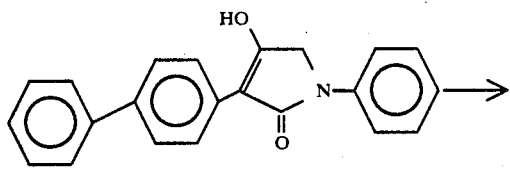
Ii

-continued 1,5-dihydro-4-(N-methylhydroxylamino)-3-(2-naphthyl)-1-phenyl-2H-pyrrol-2-one (Ij)

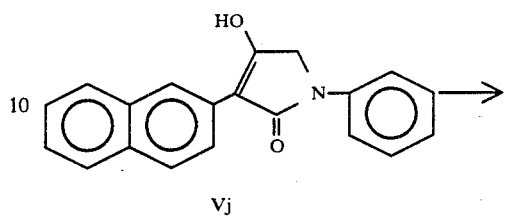
Vj

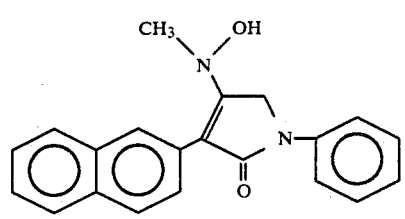
Ij 3-(4-benzyloxyphenyl)-1,5-dihydro-4-(N-methylhydroxylamino)-1-(3-pyridyl)-2H-pyrrol-2-one (Ik)

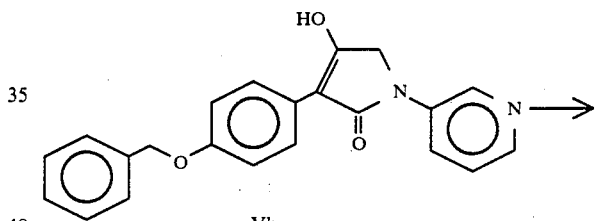
Vk

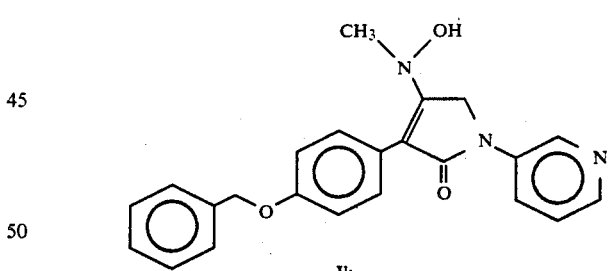
Ik 1,5-dihydro-4-(N-methylhydroxylamino)-3-(4-phenoxy-phenyl)-1-(3-pyridyl)-2H-pyrrol-2-one (Il)

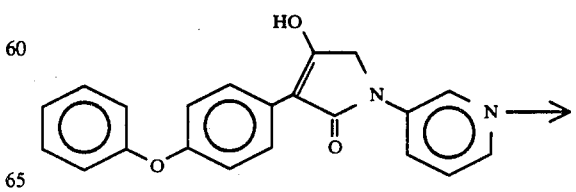
Vl

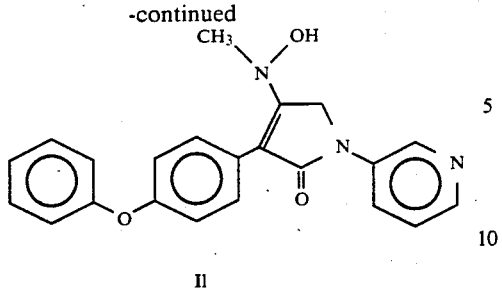

Il

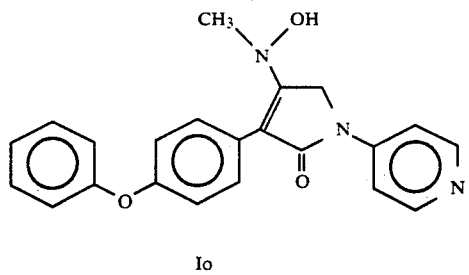

Io 3-(2-dibenzofuranyl)-1,5-dihydro-4-(N-methylhydroxyl-amino)-1-(3-pyridyl)-2H-pyrrol-2-one (Im)

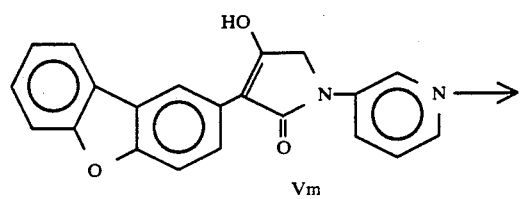

Vm 3-(2-dibenzofuranyl)-1,5-dihydro-4-(N-methylhydroxyl-amino)-1-(4-pyridyl)-2H-pyrrol-2-one (Ip)

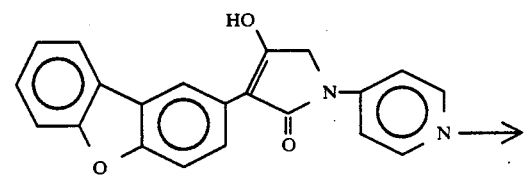

Vp

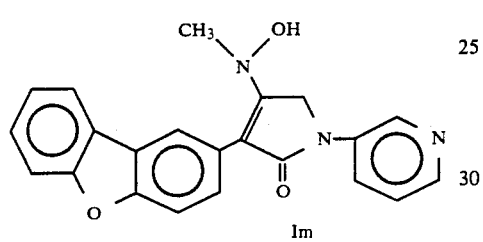

Im 3-(4-benzyloxyphenyl)-1,5-dihydro-4-(N-methylhydroxyl-amino)-1-(4-pyridyl)-2H-pyrrol-2-one (In)

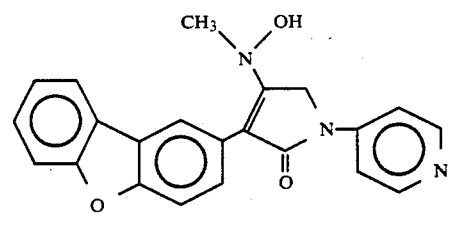

Ip

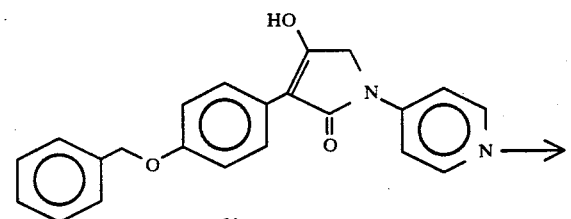

Vn 3-(4-benzyloxyphenyl)-1,5-dihydro-4-(N-methylhydroxyl-amino)-1-(4-methylthiophenyl)-2H-pyrrol-2-one (Iq)

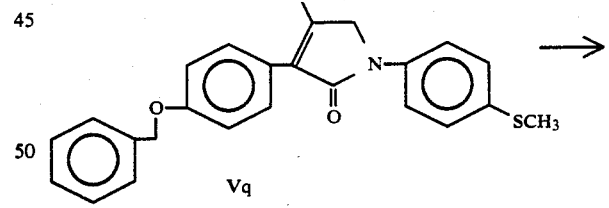

Vq

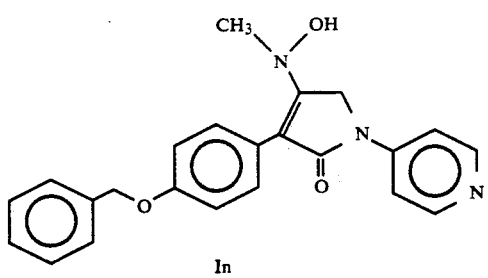

In 1,5-dihydro-4-(N-methylhydroxylamino)-3-(4-phenoxy-phenyl)-1-(4-pyridyl)-2H-pyrrol-2-one (Io)

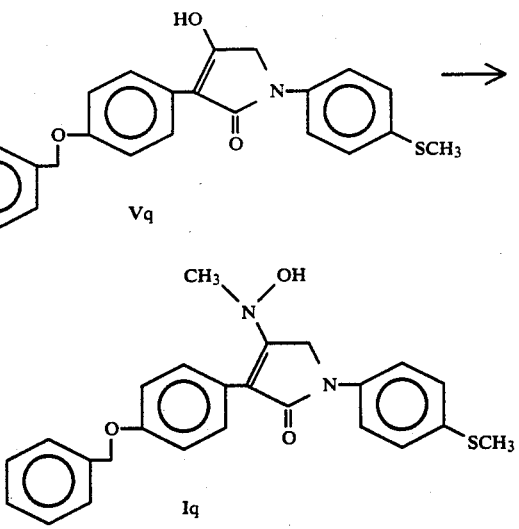

Iq

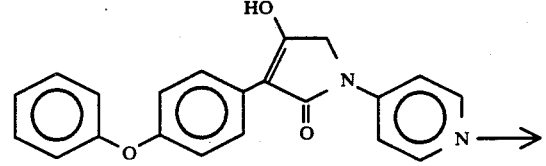

Vo 1,5-dihydro-4-(N-methylhydroxylamino)-1-(4-methylthio-phenyl)-3-(4-phenoxyphenyl)-2H-pyrrol-2-one (Ir)

-continued

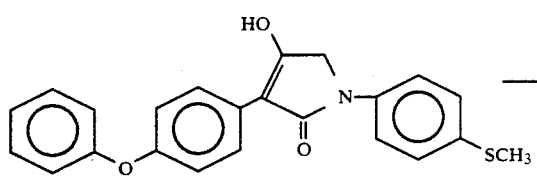
Vr

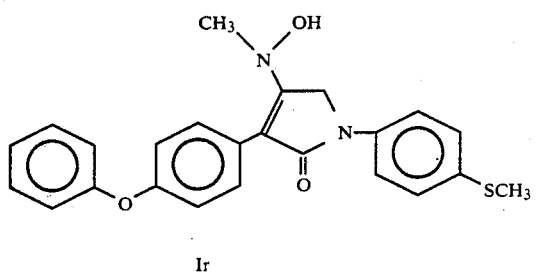
Ir 3-(2-dibenzofuranyl)-1,5-dihydro-4-(N-methylhydroxyl-amino)-1-(4-methylthiophenyl)-2H-pyrrol-2-one (Is)

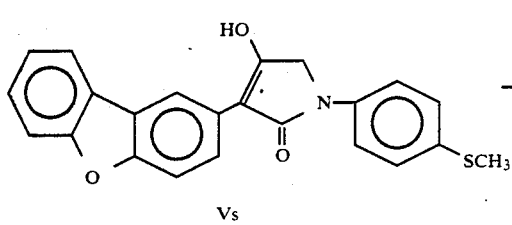
Vs

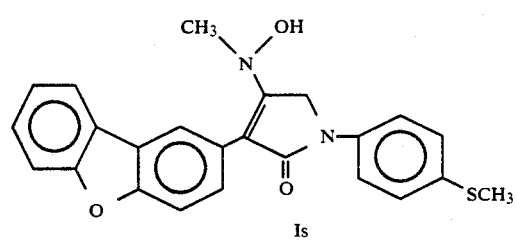
Is 3-(4-benzyloxyphenyl)-1,5-dihydro-4-(N-methylhydroxyl-amino)-1-(4-methylsulfinylphenyl)-2H-pyrrol-2-one (It)

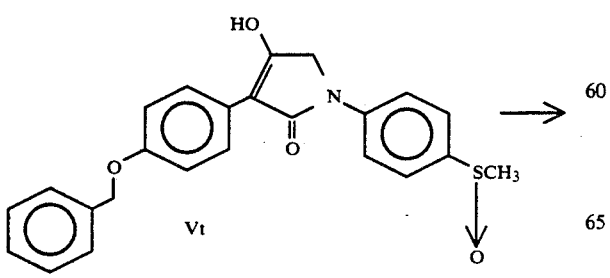
Vt

-continued

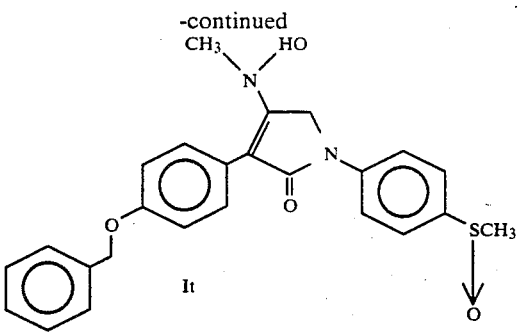
It 1,5-dihydro-4-(N-methylhydroxylamino)-1-(4-methyl-sulfinylphenyl)-3-(4-phenoxyphenyl)-2H-pyrrol-2-one (Iu)

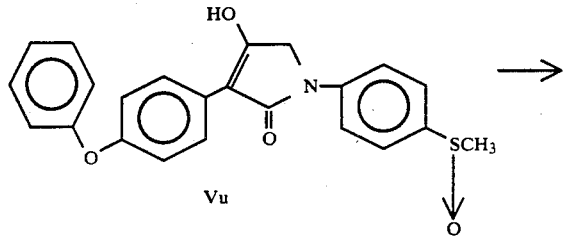
Vu

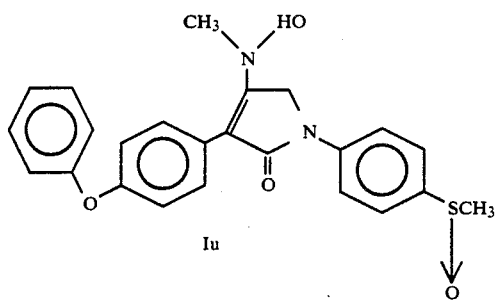
Iu 3-(2-dibenzofuranyl)-1,5-dihydro-4-(N-methyl-hydroxylamino)-1-(4-methylsulfinylphenyl)-2H-pyrrol-2-one (Iv)

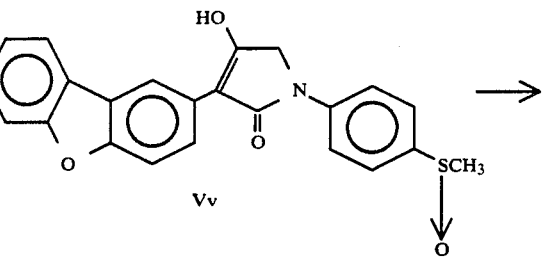
Vv

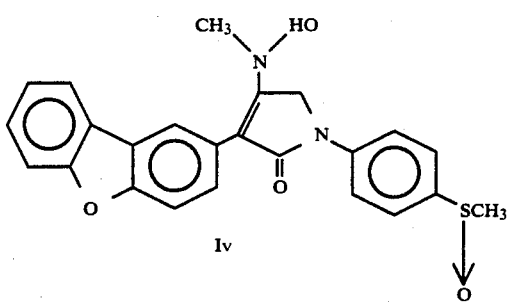
Iv

SYNTHETIC ROUTE B

EXAMPLE 4

Ethyl N-phenylglycinate

To a 250 mL round-bottom flask equipped with addition funnel and argon inlet was added 50 mL of aniline III which was stirred mechanically at 0° C. under argon atmosphere. Ethyl bromoacetate, 25 mL (224 mmol) was added in dropwise fashion over 60 min. The mixture slowly solidified and was allowed to stand unstirred at −25° C. for 18 hours. The solid was chipped from the flask and partitioned between dichloromethane ($CH_2Cl_2$) and water. The aqueous layer was made basic with 20 mL 50 NaOH solution and extracted with $CH_2Cl_2$. The combined organic layers were washed well with $H_2O$, dried over $MgSO_4$ and concentrated. The residue was crystallized from hexane containing a trace of $CH_2Cl_2$. Total yield was 28 g (156 mmol, 70% yield) based on ethyl bromoacetate used. mp. 54°–55° C., $^1$H-NMR ($CDCl_3$) ppm δ7.19 (t, 2H, J=7 Hz), 6.76 (t, 1H, J=7 Hz), 6.60 (d, 1H, J=7 Hz), 4.24 (q, 2H, J=7 Hz), 3.89 (S, 2H), 1.29 (t, 3H, J=7 Hz; IR (KBr) 3420, 1742, 1610, 1520, 1220 $cm^{-1}$.

Calcd. for $C_{10}H_{13}NO_2$: % C=67.02, % H=7.31, % N=7.82". Found: % C=66.78, % H=7.36, % N=7.74.

By substituting the indicated starting materials for IIIa and following the procedure set forth in example 4 above, the following compounds VI can be produced:

Ethyl N-methylglycinate (VIb)

$$EtO_2CCH_2Br + H_2NCH_3 \longrightarrow EtO_2CCH_2NCH_3$$
$$\text{IIIb} \qquad \qquad \qquad \text{VIb}$$

Ethyl N-(3-pyridyl)glycinate (VIc)

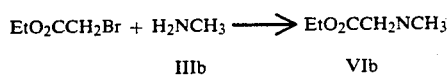
IIIc

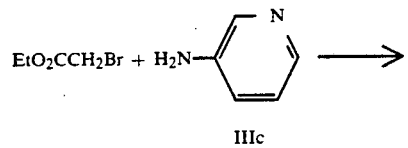
VIc

Ethyl N-(4-pyridyl)glycinate (VId)

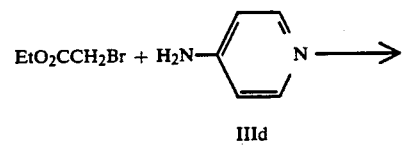
IIId

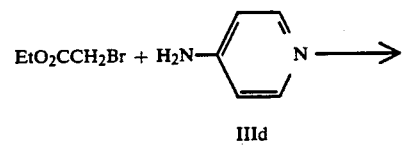
VId

Ethyl N-(4-methylthiophenyl)glycinate (VIe)

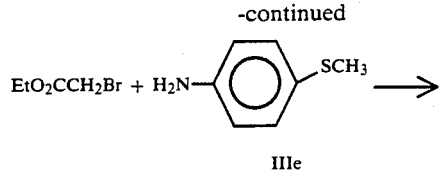
IIIe

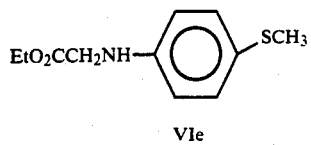
VIe

EXAMPLE 5

Ethyl N-phenyl-N-(2-phhenylcacetyl)glycinate (VIIa)

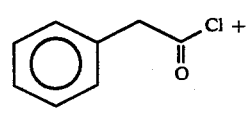
IIa

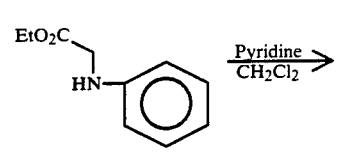

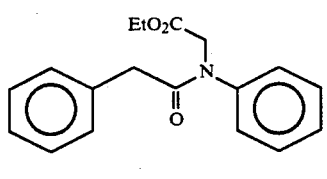
VIIa

To a stirred solution of 4.5 g (25 mmol) Ethyl N-phenylglycinate, VIa, and 3 mL dry pyridine in 25 mL dry $CH_2Cl_2$ under argon atmosphere at 25° C. was added 3.3 mL (25 mmol) of phenylacetyl chloride, IIa, via syringe over 15 min.

An exotherm was observed. After stirring for 12 hours, the mixture was poured into 100 mL 10% HCl and extracted with 150 mL ethyl-acetate. The organic extract was washed with a saturated solution of $NaHCO_3$ and brine, was dried over $MgSO_4$, filtered, and concentrated to give 8.0 g (ca 100% yield) of a light brown oil.

$^1$H-NMR ($CDCl_3$) ppm δ7.4–7.0 (m, 10H), 4.31 (s, 2H), 4.12 (q, 2H, J=7 Hz), 3.47 (s, 2H), 1.23 (t, 3H, J=7 Hz).

By substituting the starting materials indicated below, for IIa and VIa and following the procedure set forth in example 5 above, the following compounds VII can be prepared:

Ethyl N-(2-(4-benzyloxyphenyl)acetyl)glycinate (VIIb)

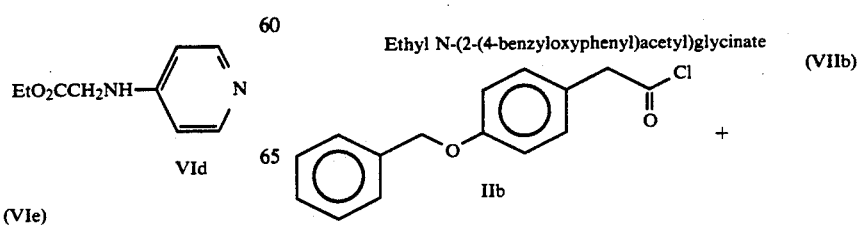
IIb

-continued

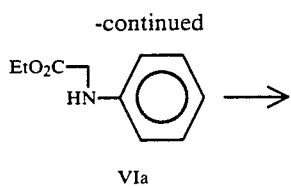

VIa

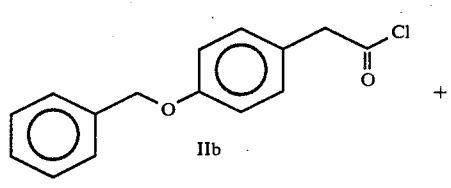

VIIb

Ethyl N-(2-(4-benzyloxyphenyl)acetyl-N-methyl-glycinate

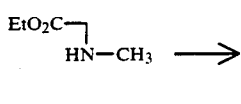
(VIIc)
IIb
+

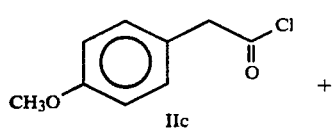

VIb

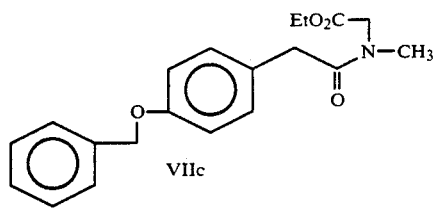

VIIc

Ethyl N-(2-(4-methoxyphenyl)acetyl-N-phenyl-glycinate

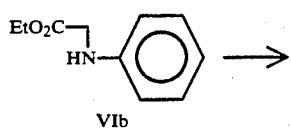
(VIId)
IIc
+

EtO$_2$C—
HN—〈phenyl〉 →
VIb

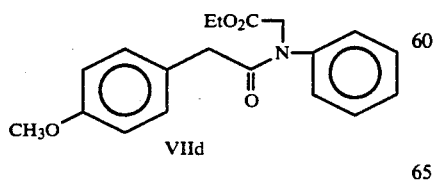

VIId

Ethyl N-(2-(4-phenoxyphenyl)acetyl)-N-phenyl-glycinate

-continued

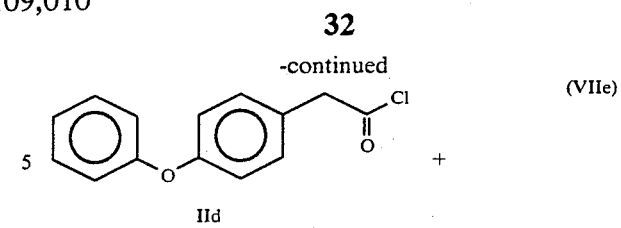
(VIIe)
IId
+

EtO$_2$C—
HN—〈phenyl〉 →
VIa

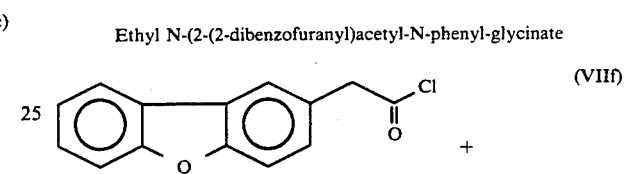

VIIe

Ethyl N-(2-(2-dibenzofuranyl)acetyl-N-phenyl-glycinate

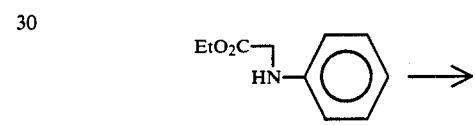
(VIIf)
IIe
+

EtO$_2$C—
HN—〈phenyl〉 →
VIa

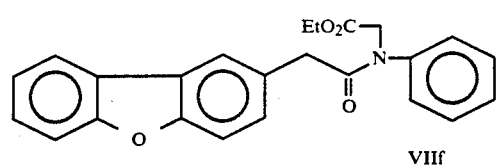

VIIf

Ethyl N-(2-(4-chlorophenyl)acetyl)-N-phenyl-glycinate

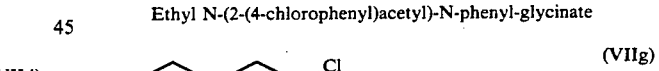
(VIIg)
IIf
+

EtO$_2$C—
HN—〈phenyl〉 →
VIa

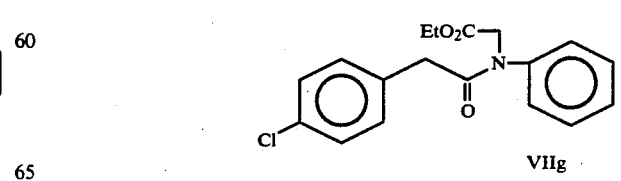

VIIg

Ethyl-N-phenyl N-(2-(4-trifluoromethyl)phenyl)-acetylglycinate

-continued
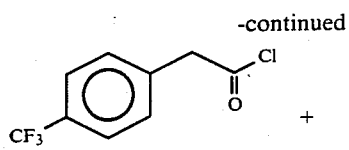
IIg
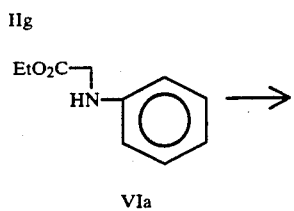
VIa
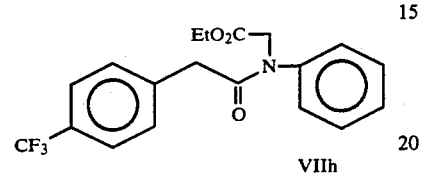
VIIh
Ethyl N-(2-(4-biphenyl)acetyl)-N-phenylglycinate (VIIi)
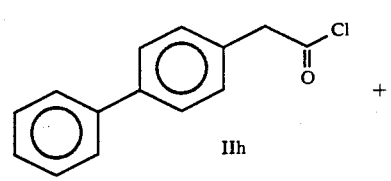
IIh
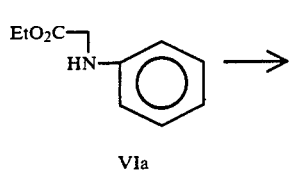
VIa
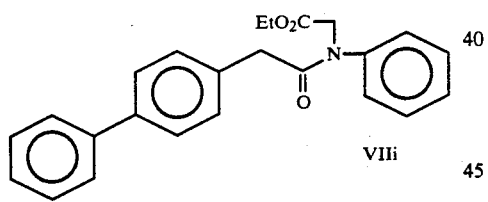
VIIi
Ethyl N-(2-(2-naphthyl)acetyl)-N-phenylglycinate (VIIj)
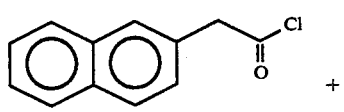
IIi
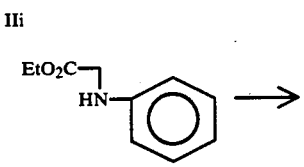
VIa
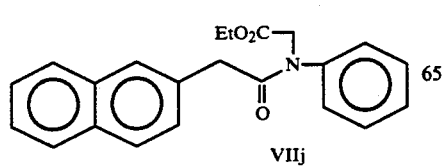
VIIj
-continued
Ethyl N-(2-(4-benzyloxyphenyl)acetyl)-N-(3-pyridyl)-glycinate (VIIk)
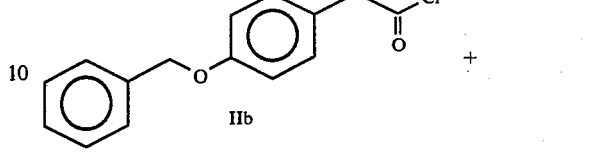
IIb
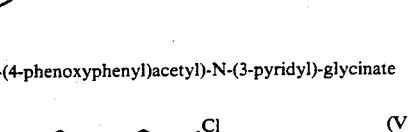
VIc
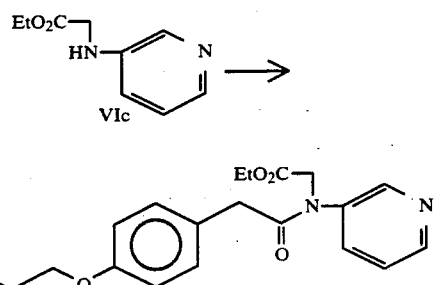
VIIk
Ethyl N-(2-(4-phenoxyphenyl)acetyl)-N-(3-pyridyl)-glycinate (VIII)
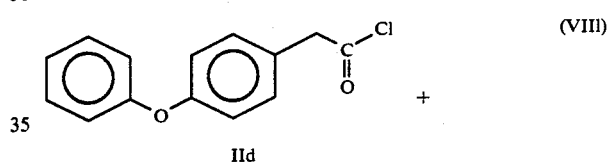
IId
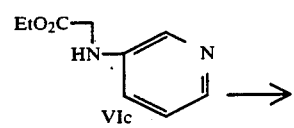
VIc
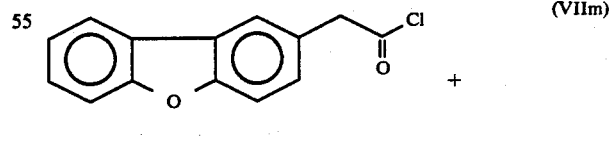
VIII
Ethyl N-(2-(2-dibenzofuranyl)acetyl)-N-(3-pyridyl)-glycinate (VIIm)
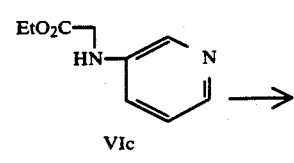
IIe
VIc -continued

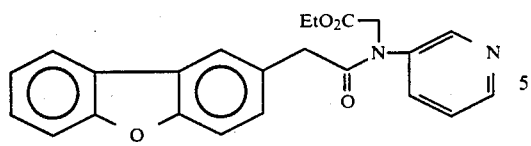
VIIm

Ethyl N-(2-(4-benzyloxyphenyl)acetyl)-N-(4-pyridyl)-glycinate

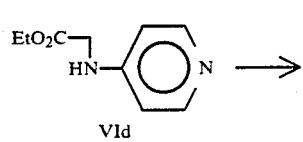 (VIIn)

+

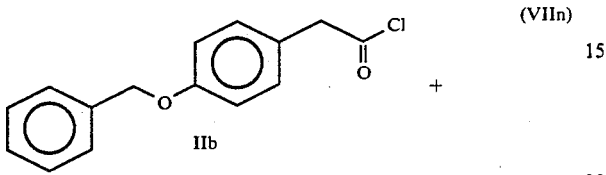
VId →

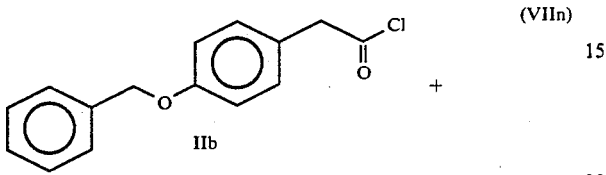
VIIn

Ethyl N-(2-(4-phenoxyphenyl)acetyl)-N-(4-pyridyl)-glynicate

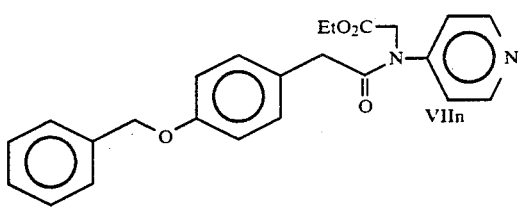 (VIIo)
IId

+

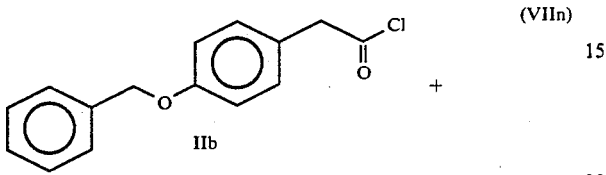
VId →

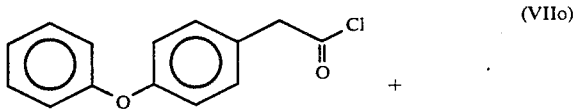
VIIo

Ethyl N-(2-(2-dibenbzofuranyl)acetyl)-N-(4-pyridyl)-glycinate

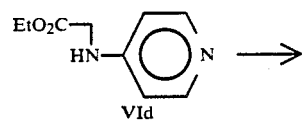 (VIIp)
IId

+

-continued

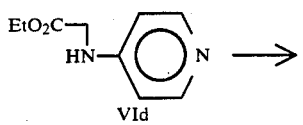
VId →

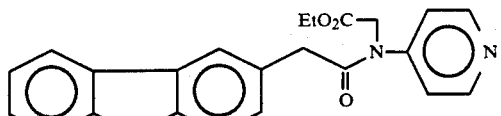
VIIp

Ethyl N-(2-(4-benzyloxyphenyl)acetyl)-N-(4-methyl-thiophenyl) glycinate

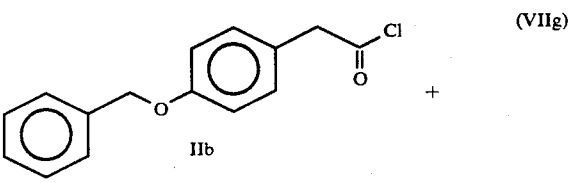 (VIIq)
IIb

+

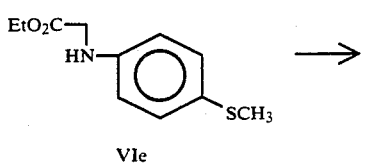
VIe →

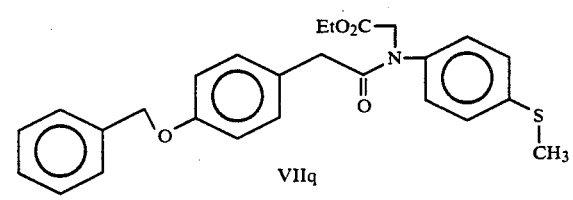
VIIq

Ethyl N-(4-methylthiophenyl)-N-(2-(4-phenoxyphenyl)-acetyl) glycinate

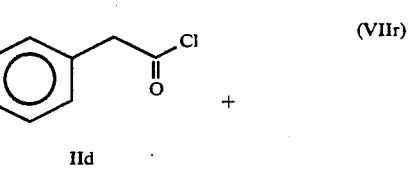 (VIIr)
IId

+

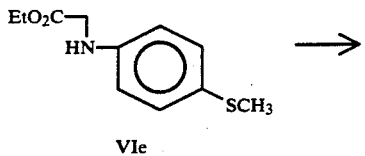
VIe →

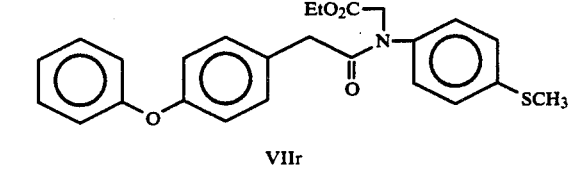
VIIr

Ethyl N-(2-(2-dibenzofuranyl)acetyl)-N-(4-methyl-thiophenyl) glycinate

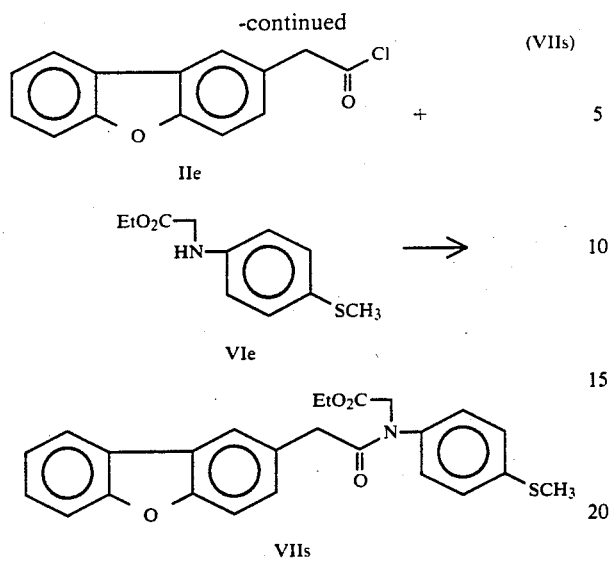

EXAMPLE 6

Ethyl N-(2-(4-benzyloxyphenyl)acetyl)-N-(4-methylsulfinylphenyl)glycinate (VIIt)

To a stirred solution of 1.34 g (2.98 mmols) of ethyl N-(2-(4-benzyloxyphenyl)acetyl)-N-(4-methylthiophenyl)glycinate (VIIq) in 25 mL dry dichloromethane ($CH_2Cl_2$) was added 1.05 equivalents of m-chloroperoxybenzoic acid at 0° C. After stirring for 30 min., the solution was poured into 200 mL of saturated $NaHCO_3$ solution containing 10 mL of 10% $NaHCO_3$ solution and was extracted with two 100 mL portions of $CH_2Cl_2$. The combined organic extracts were dried over $MgSO_4$ and concentrated to give 1.40 g (ca. 100% yield) of the sulfoxide (VIIt) was an oil.

By substituting the indicated material for (VIIq) and following the procedure set forth in Example (6) above, the following compounds can be produced.

Ethyl N-(4-methylsulfinylphenyl-N-(2-(4-phenoxyphenyl)acetyl)glycinate (VIIu)

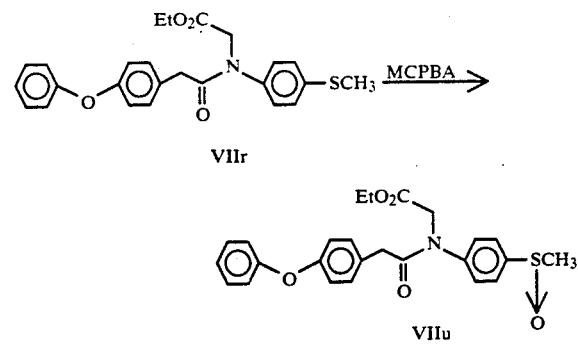

Ethyl N-(2-(2-dibenzofuranyl)acetyl)-N-(4-methylsulfinylphenyl)glycinate (VIIv)

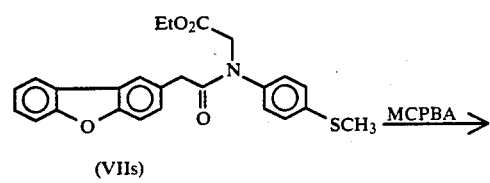

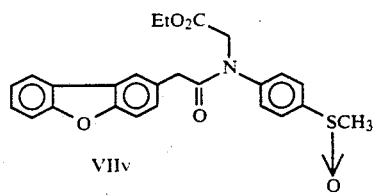

EXAMPLE 7

1,5-dihydro-1,3-diphenyl-4-hydroxy-2H-pyrrol-2-one (Va)

To a 250 mL round-bottom flask equipped with addition funnel, condenser, magnetic sitrring bar and argon inlet was added 3.0 g (80 mmol) of 60% sodium hydride in mineral oil. The solid was washed twice with hexane then covered with 70 mL tetrahydrofuran. To the stirred suspension was added a solution of 7.5 g (25 mmol) of Ethyl N-phenyl-N-(2-phenylacetyl)glycinate (VIIa) in 30 mL dry THF. Ethyl alcohol (2-drops) was added and the reaction was warmed carefully to reflux under argon. An exotherm and rapid hydrogen evolution was observed. After heating for 2 hours, the reaction mixture was quenched with water, and partitioned between ethylacetate (100 mL) and water (200 mL). The aqueous layer was acidified to pH=2 and the precipitate was filtered and vacuum dried to give 5.05 g (20 mmol, 80% yield) of a solid.

mp 293°–295° C. (dec), $^1$H-NMR (DMSO) ppm δ7.99 (d, 2H, J=6 Hz), 7.73 (d, 2H, J=6 Hz), 7.37 (t, 4H, J=6 Hz), 7.19 (t, 1H, J=6 Hz), 7.05 (t, 1H, J=6 Hz), 4.48 (S, 2H); IR (KBr) 3500–2400 (b, OH), 1620, 1400 $cm^{-1}$.

By substituting the indicated starting material, VII, for VIIa and following the procedure set forth in Example 7 above, the following compounds V can be produced.

3-(4-(benzyloxyphenyl)-1,5-dihydro-4-hydroxy-1-phenyl-2H-pyrrol-2-one (Vb)

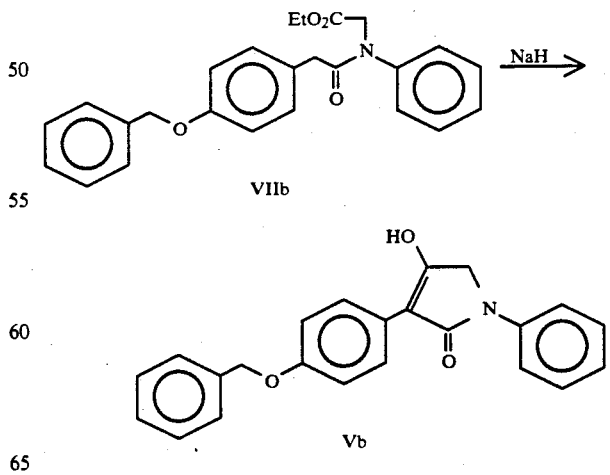

3-(4-benzyloxyphenyl)-1,5-dihydro-4-hydroxy-1-methyl-2H-pyrrol-2-one (Vc)

-continued

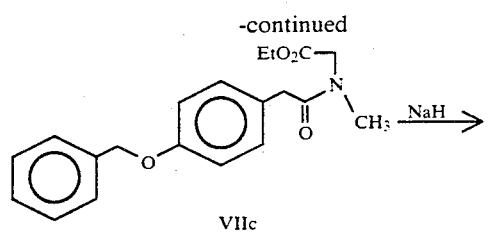

VIIc

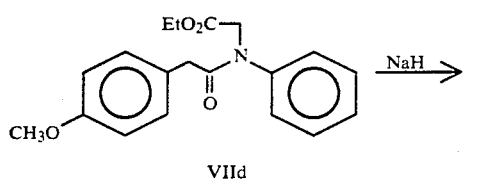

Vc 1,5-dihydro-4-hydroxy-3-(4-methoxyphenyl)-1-phenyl-2H-pyrrol-2-one (Vd)

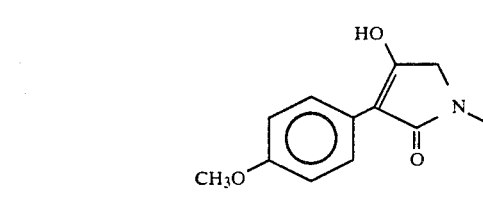

VIId

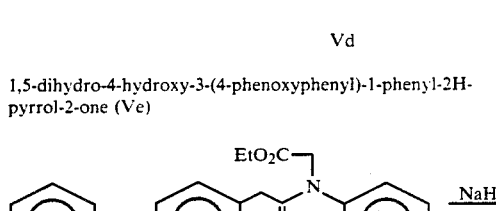

Vd 1,5-dihydro-4-hydroxy-3-(4-phenoxyphenyl)-1-phenyl-2H-pyrrol-2-one (Ve)

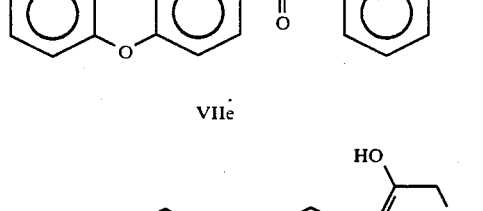

VIIe

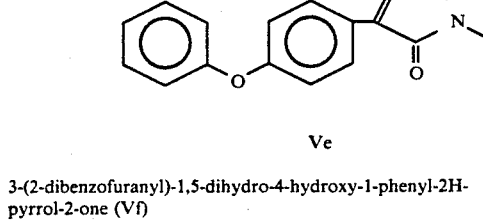

Ve 3-(2-dibenzofuranyl)-1,5-dihydro-4-hydroxy-1-phenyl-2H-pyrrol-2-one (Vf)

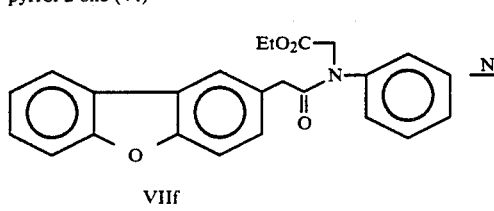

VIIf

-continued

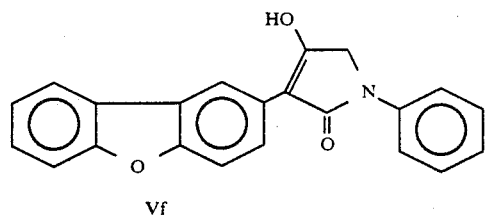

Vf 3-(4-chlorophenyl)-1,5-dihydro-4-hydroxy-1-phenyl-2H-pyrrol-2-one (Vg)

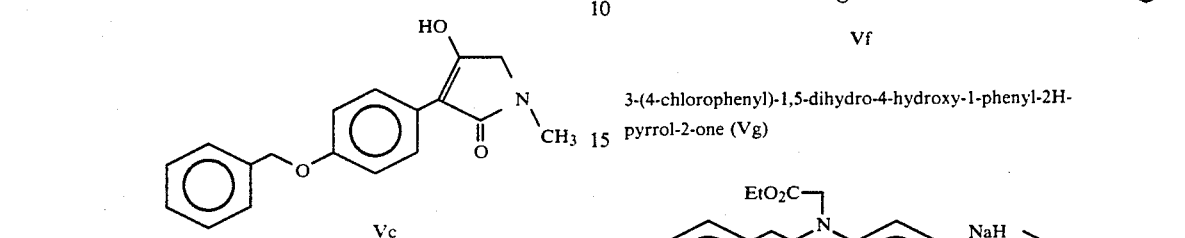

VIIg

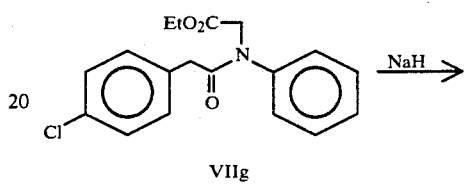

Vg 1,5-dihydro-4-hydroxy-1-phenyl-3-(4-trifluoro-methylphenyl)-2H-pyrrol-2-one (Vh)

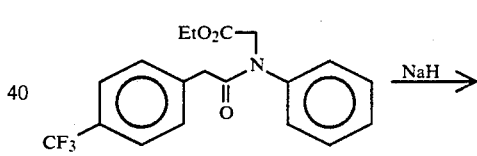

VIIh

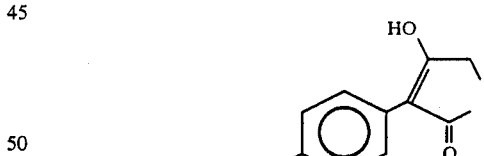

Vh 3-(4-biphenyl-1,5-dihydro-4-hydroxy-1-phenyl-2H-pyrrol-2-one (Vi)

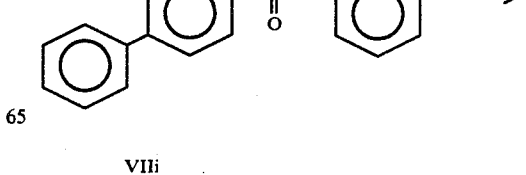

VIIi

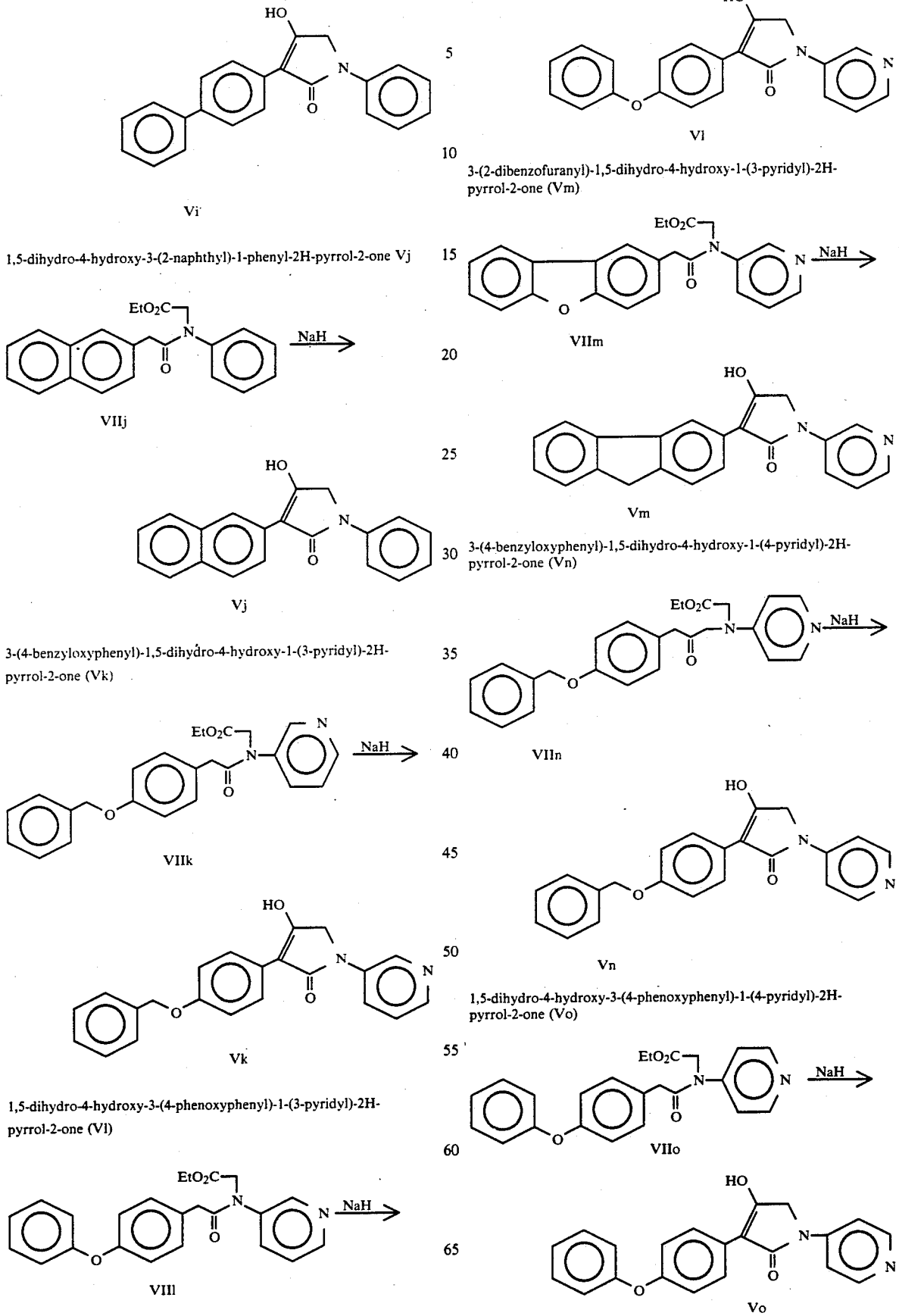

3-(2-dibenzofuranyl)-1,5-dihydro-4-hydroxy-1-(4-pyridyl)-2H-pyrrol-2-one (Vp)

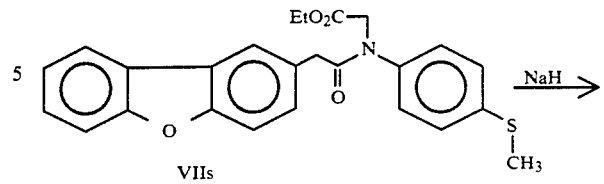

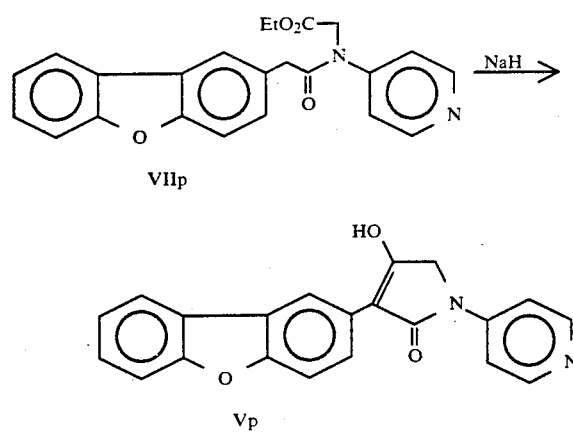

3-(4-benzyloxyphenyl)-1,5-dihydro-4-hydroxy-1-(4-methylthiophenyl)-2H-pyrrol-2-one (Vq)

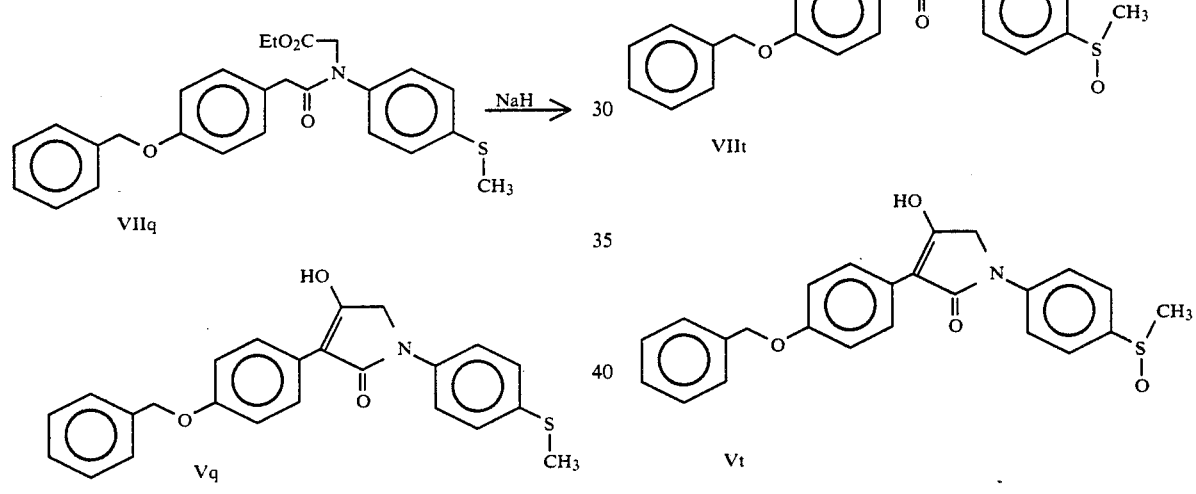

1,5-dihydro-4-hydroxy-1-(4-methylthiophenyl)-3-(4-phenoxyphenyl)-2H-pyrrol-2-one (Vr)

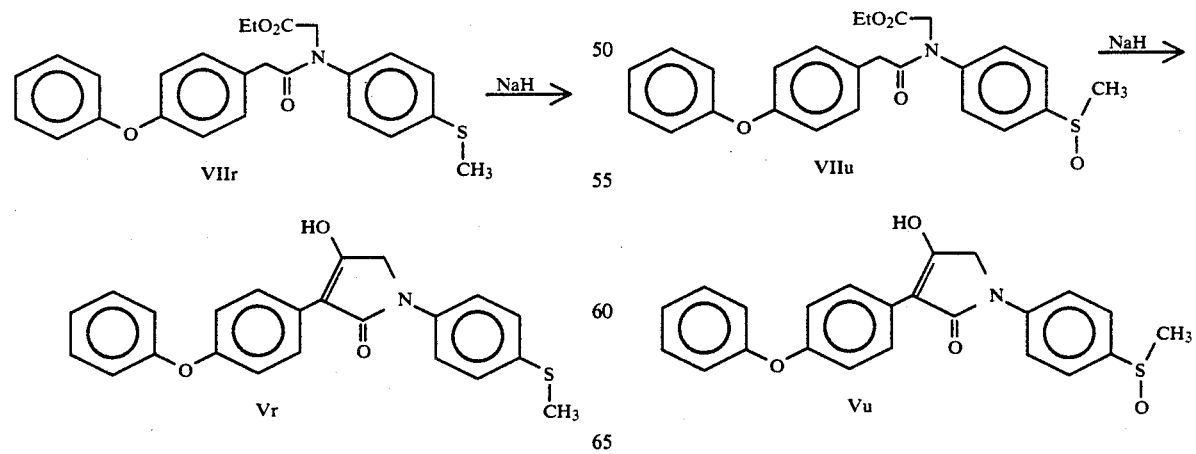

3-(2-dibenzofuranyl)-1,5-dihydro-4-hydroxy-1-(4-methylthiophenyl)-2H-pyrrol-2-one (Vs)

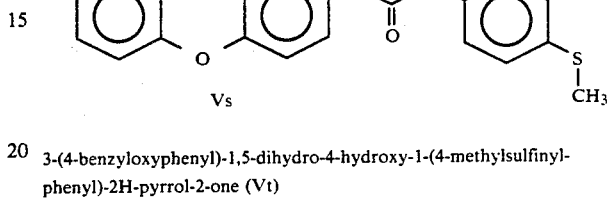

3-(4-benzyloxyphenyl)-1,5-dihydro-4-hydroxy-1-(4-methylsulfinylphenyl)-2H-pyrrol-2-one (Vt)

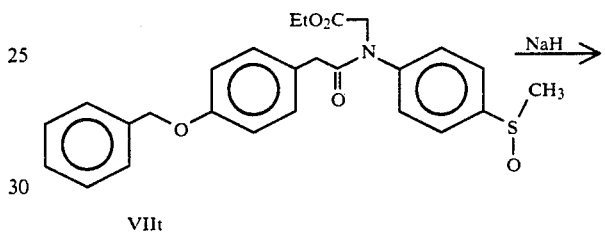

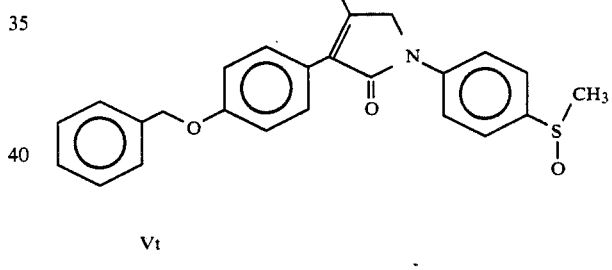

1,5-dihydro-4-hydroxy-1-(4-methylsulfinylphenyl)-3-(4-phenoxyphenyl)-2H-pyrrol-2-one (Vu)

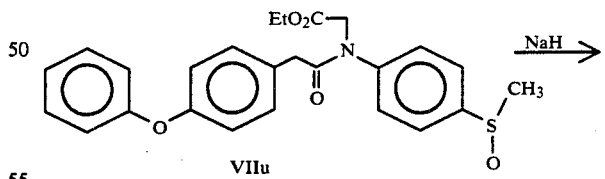

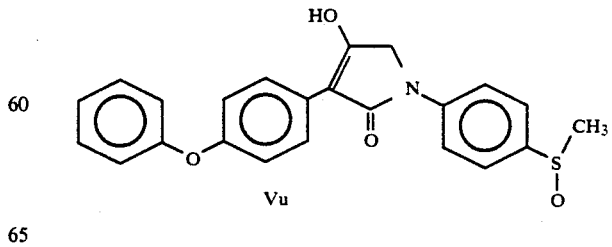

3-(2-dibenzofuranyl)-1,5-dihydro-4-hydroxy-1-(4-methylsulfinylphenyl)-2H-pyrrol-2-one (Vv)

-continued

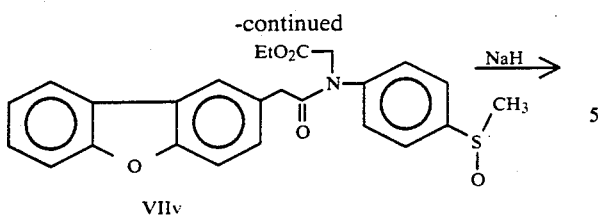

VIIv

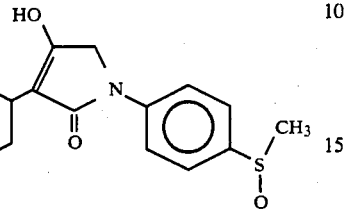

Vv

EXAMPLE 8

4-Phenoxyphenylacetic acid

The procedure of McKillop et al. (J. Am. Chem. Soc. 95, 3340 (1973)) was followed. To a solution of 40.5 g (91.1 mmol) of thallium trinitrate trihydrate (TTN) in 200 mL dry methyl alcohol was cautiously added 8 mL trifluoromethanesulfonic acid followed by 17.3 g (81.6 mmol) of 4-phenoxyacetophenone. After several minutes of stirring at 25° C., a white precipitate formed. Stirring under argon atmosphere was continued for 6 hours. The reaction mixutre was cautiously poured into 200 mL sat. $K_2CO_3$ solution and extracted with two 200 mL portions of 1:1 ethyl acetate/hexane. The combined extracts were washed with three 100 mL portions of brine, dried over $MgSO_4$, filtered, and concentrated to give 19.5 g of an oil. Distillation under high vacuum gave 15 g (69 mmol, 76% yield) of a colorless oil, bp. 125°-128° C. at 20μ Hg; $^1$H-NMR ($CDCl_3$) ppm δ7.34 (t, 2H, J=7 Hz), 7.25 (d, 2H, J=8 Hz), 7.11 (t, 1H, J=7 Hz), 7.03-6.95 (m, 4H), 3.71 (s, 3H), 3.61 (s, 2H).

Calcd. for $C_{15}H_{14}O_3$: % C=74.36, % H=5.82. Found: % C=74.41, % H=5.8.

The above methyl ester was (60 mmol) was dissolved in 100 mL methyl alcohol and treated with 2.8 g (100 mmol) solid lithium hydroxide (LiOH) with stirring at 25° C. and argon for 24 hours. Addition of 100 mL 1N HCl afforded a precipitate which was filtered and vacuum dried to give 13.8 g (65 mmols) of acid, mp 74°-77° C.

By substituting the indicated material for 4-phenoxyacetophenone and following the procedure set forth in example 8 above, the following compounds can be produced.

2-dibenzofuranylacetic acid

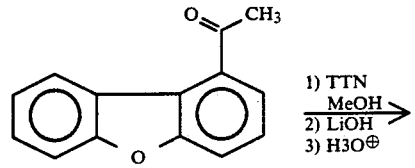

-continued

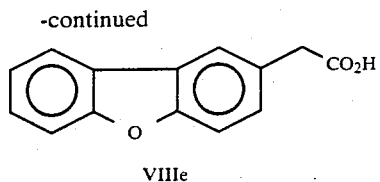

VIIIe

EXAMPLE 9

4-benzyloxyphenylacetic acid

To a stirred slurry of 10 g (200 mmol) 60% NaH in oil (which had been washed with hexane) in 100 mL dry DMF under $N_2$ atmosphere at 25° C. was added a solution of 15.2 g (100 mmol) of 4-hydroxyphenylacetic acid in 100 mL dry DMF over a 30 min. period. After addition was complete, the mixture was heated at 50° C. for 6 hours, 23.8 mL of benzyl bromide (200 mmol) was added at 40° C. and the mixture was stirred at 25° C. for 48 hours. The solvent was removed in vacuo and the residue partitioned between 400 mL EtOAc and 100 mL $H_2O$. The organic extract was washed repeatedly with H2O, dried over MgSO4 and concentrated to give 34 g of a tan solid. the crude ether ester was dissolved in 200 mL 95% EtOH and 8 g (200 mmol) solid NaOH was added. The solution was refluxed for 10 hours and the excess solvent was removed in vacuo. The residue was dissolved in $H_2O$, washed with ether, filtered, and acidified to pH=2. The solid was collected and vacuum dried to give 20.1 g (85 mmol) of acid; $^1$H-NMR (DMSO) ppm δ7.31 (m, 5H) 7.14 (d, 2H, J=7 Hz), 6.84 (d, 2H, J=7 Hz), 5.15 (bs, 1H), 5.02 (s, 2H), 3.39 (s, 2H).

EXAMPLE 10

4-benzyloxyphenylacetyl chloride (IIb)

A stirred mixture of 11.7 (50 mmol) of 4-benzyloxyphenylacetic acid VIIIb in 25 mL dichloromethyl methyl ether was stirred at reflux for 18 hours. The cooled solution was filtered and concentrated under high vacuum to give 13.1 g (ca. 100% yield) of crude acid chloride as a light tan solid IIb. $^1$H-NMR ($CDCl_3$) ppm δ7.35 (m, 5H), 7.21 (d, 2H, J=7 Hz), 6.95 (d, 2H, J=7 Hz), 5.00 (s, 2H), 4.00 (s, 2H).

By substituting the indicated material for IIb and following the procedure set forth in example 10 above, the following compounds II can be prepared.

4-methoxyphenylacetyl chloride (IIc)

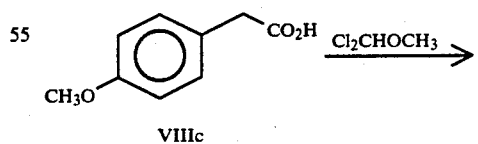

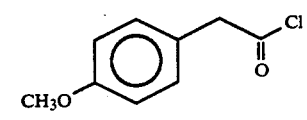

4-phenoxyphenylacetyl chloride (IId)

-continued

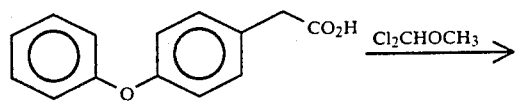

VIIId

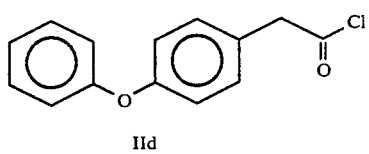

IId 2-dibenzofuranylacetyl chloride (IIe)

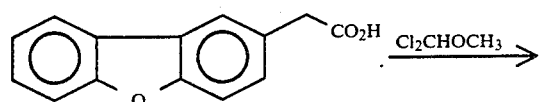

VIII

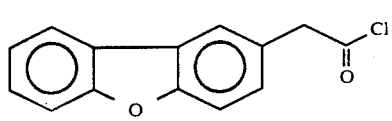

IIe 4-chlorophenylacetyl chloride (IIf)

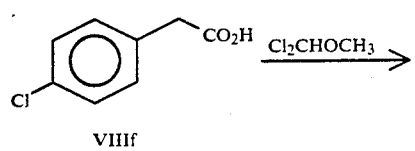

VIIIf

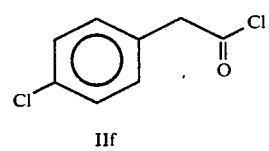

IIf (α,α,α-trifluoro-p-tolyl)acetyl chloride (IIg)

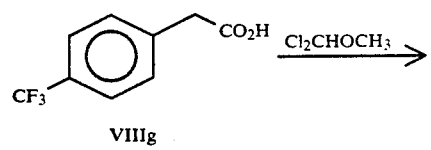

VIIIg

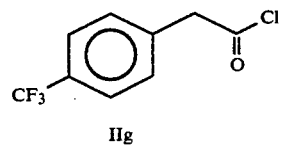

IIg 4-biphenylacetyl choride (IIh)

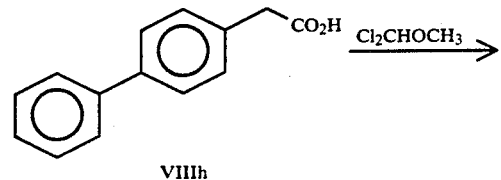

VIIIh

-continued

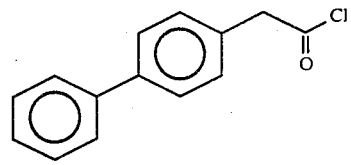

IIh 2-naphthylacetyl chloride (IIi)

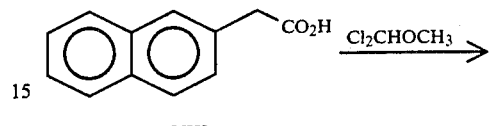

VIII

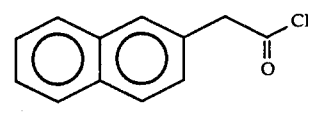

IIi

The compounds of this invention are useful both in the free acid or base form and as salts. The expression "a salt thereof" means any organic or inorganic addition salt of the compounds of formula I. These salts are included within the scope of this invention. Such salts include, for example, those formed with the following acids: hydrochloric, hydrobromic, sulfonic, sulfuric, phosphoric, nitric, ascorbic, methanesulfonic, acetic, propionic, tartaric, citric, lactic, malic, mandelic, cinnamic, palmitic, itaconic, fumaric, benzenesulfonic and toluenesulfonic. The non-toxic, physiologically acceptable salts are preferred, although other salts are also useful for, for example, isolating or purifying the product.

The salts of the foregoing compounds can be formed by conventional means such as by reacting the free acid forms of the product with one or more equivalents of the appropriate base in a solvent or medium in which the salt is insoluble, or in a solvent such as water which is then removed in vacuo or by freeze drying. A salt could also be formed by exchanging the cations of an existing salt for another cation on a suitable ion exchange resin.

The utility of the compounds of this invention are useful as selective lipoxygenase inhibitors. 5-Lipoxygenase (5-LO) facilitates the generation of 5,12-dihydroxyeicosatetraenoic acid, known as leukotirene $B_4$ ($LTB_4$). When 5-LO is inhibited, a decreased amount of $LTB_4$ is generated. Therefore, by measuring the amount of $LTB_4$ generated in whole blood of laboratory animals after treatment with compounds of this invention, 5-LO inhibition can be determined.

The following procedures have been used to evaluate the compounds of this invention as 5-LO inhibitors. The test compound was added to blood samples taken from F-344 rats. The samples were incubated for 10 minutes at 37° F. The samples were then stimulated with 30 micro Molar calcium ionophore, A23187, and incubated for another 30 minutes. Enzymatic activity was stopped by the addition of ice cold saline, and the cells were removed by centrifugation at 28,000 g-minutes. Protein was precipitated with methanol (aqueous:methanol, 2:1), and then adjusted to 15% methanol by the addition of water. The supernatant was extracted on Bond Elut C18 solid phase extraction columns. Samples were washed on the columns with 15% methanol and eluted with 100% methanol. The methanolic extracts were diluted to 75% methanol with water and the $LTB_4$ was quantitated by HPLC (C18 column, 75% methanol:25% water:0.01% trifluroacetic acid) and the per cent inhibition of 5-LO in vitro was calculated.

Similarly, when compounds were tested for activity ex vivo, the above procedure was followed except that the animals were given the test compound either intravenously (iv) or orally (po) before blood samples were collected. Blood was collected from the dosed animals at various time periods after dosing, and then treatment of the samples was the same as the in vitro procedure described above. The results of this in vitro and ex vivo testing are illustrated in Table I below.

TABLE 1

5-LO INHIBITION

| *Compound | Route | Species | Dose | Time | % Inih. ± SE |
|---|---|---|---|---|---|
| 1 | in vitro | rat | 10 uM | 10 min | 27 ± 3 |
| 2 | in vitro | rat | 10 uM | 10 min | 68 ± 3 |
| 2 | ex vivo, iv | rat | 10 mg/Kg | 5 min | 42 ± 5 |
| 2 | ex vivo, iv | rat | 10 mg/Kg | 30 min | 30 ± 9 |
| 2 | ex vivo, iv | rat | 10 mg/Kg | 60 min | 14 ± 9 |
| 3 | in vitro | rat | 10 uM | 10 min | 100 ± 0 |
| 3 | in vitro | mouse | 10 uM | 10 min | 84 ± 2 |
| 3 | in vitro | mouse | 30 uM | 10 min | 100 ± 0 |
| 3 | in vitro | mouse | 100 uM | 10 min | 100 ± 0 |
| 3 | in vitro | g. pig | 10 uM | 10 min | 60 ± 4 |
| 3 | in vitro | g. pig | 30 uM | 10 min | 95 ± 5 |
| 3 | in vitro | g. pig | 100 uM | 10 min | 100 ± 0 |
| 3 | in vitro | human | 0.3 uM | 5 min | −4 ± 3 |
| 3 | in vitro | human | 1.0 uM | 5 min | −3 ± 4 |
| 3 | in vitro | human | 3.0 uM | 5 min | 11 ± 3 |
| 3 | in vitro | human | 10.0 uM | 5 min | 58 ± 14 |
| 3 | ex vivo, iv | rat | 10 mg/Kg | 5 min | 100 ± 0 |
| 3 | ex vivo, iv | rat | 10 mg/Kg | 30 min | 62 ± 4 |
| 3 | ex vivo, iv | rat | 10 mg/Kg | 60 min | 33 ± 5 |
| 3 | ex vivo, po | rat | 100 mg/Kg | 5 min | 9 ± 4 |
| 3 | ex vivo, po | rat | 100 mg/Kg | 30 min | 16 ± 8 |
| 3 | ex vivo, po | rat | 100 mg/Kg | 60 min | −9 ± 8 |
| 3 | ex vivo, po | rat | 30 mg/Kg | 10 min | 18 ± 3 |
| 3 | ex vivo, po | rat | 100 mg/Kg | 10 min | 8 ± 4 |
| 3 | ex vivo, po | rat | 300 mg/Kg | 10 min | −8 ± 7 |
| 3 | ex vivo, po | mouse | 30 mg/Kg | 10 min | 5 ± 6 |
| 3 | ex vivo, po | mouse | 100 mg/Kg | 10 min | 22 ± 2 |
| 3 | ex vivo, po | mouse | 300 mg/Kg | 10 min | 11 ± 13 |

*Compound 1: 3-(4-benzyloxyphenyl)-1,5-dihydro-1-methyl-4-(N-methylhydroxylamino)-2H-pyrrol-2-one
*Compound 2: 3-(4-benzyloxyphenyl)-1,5-dihydro-4-(N-methylhydroxylamino)-1-(4-pyridyl)-2H-pyrrol-2-one
*Compound 3: 1,5-dihydro-1,3-diphenyl-4-(N-methylhydroxylamino)-2H-pyrrol-2-one A patient, for the purpose of this invention, is a mammal, including a human, in need of treatment for a particular condition, injury or disease. The amount of active ingredient (i.e., a compound of Formula I) to be administered to a patient for the treatment of a particular condition, injury or disease can vary widely according to such considerations as the particular compound and dosage unit employed, the period of treatment, the age and sex of the patient treated, and the extent of the particular condition, injury or disease treated.

Treatment of asthma will generally be by oral or inhaled routes of administration. Treatment of rheumatoid arthritis will generally be by oral, intravenous or topical routes of administration.

The total amount of active ingredient to be administered to a patient by inhalation will generally range from about 0.1 mg/kg to 30.0 mg/kg and preferably from 1 mg/kg to 10 mg/kg. A unit dosage may contain from 5 mg to 525 mg of active ingredient, and can be taken one or more times per day. For example, a 50 kg patient may be administered 50 mg to 700 mg active ingredient, four times a day for a total dose of 200 mg-2800 mg per day.

The total amount of active ingredient to be administered intravenously will generally range from about 0.1 mg/kg to 30 mg/kg and preferably from 1.0 mg/kg to 10.0 mg/kg. A unit dosage may contain from 5 mg to 525 mg of active ingredient, and can be taken one or more times per day. For example, a 50 kg patient may be administered 50 mg-700 mg active ingredient four times a day for a total dose of 200 mg-2800 mg per day.

The total amount of active ingredient to be administered orally will generally range from 0.1 mg/kg to 100 mg/kg, and preferably from 1.0 mg/kg to 50 mg/kg. A unit dosage may contain from 5 mg to 1000 mg of active ingredient, and can be taken one or more times per day. For example, a 50 kg patient may be administered 50 mg-2500 mg of active ingredient four times a day for a total of 200 mg-10,000 mg per day.

The compounds of this invention can be utilized to achieve the desired pharmacological effect by administration to a patient in need thereof in an appropriately formulated pharmaceutical composition. Therefore, the present invention includes pharmaceutical compositions which are comprised of a pharmaceutically-acceptable carrier and a pharmaceutically-effective amount of a compound of Formula I. A pharmaceutically-acceptable carrier is any carrier which is relatively non-toxic and innocuous to a patient at concentrations consistent with effective activity of the active ingredient so that any side effects ascribable to the carrier do not vitiate the beneficial effects of the active ingredient. A pharmaceutically-effective amount of compound is that amount which produces a result or exerts an influence on the particular condition being treated. The compounds of Formula I can be administered with a pharmaceutically-acceptable carrier using conventional dosage unit forms orally, parenternally, topically, as an aerosol, or the like.

For oral administration the compounds can be formulated into solid or liquid preparations such as capsules, pills, tablets, troches, lozenges, melts, powders, solutions, suspensions, or emulsions and may be prepared according to methods known to the art for the manufacture of pharmaceutical compositions. The solid unit dosage forms can be a capsule which can be of the ordinary hard- or soft-shelled gelatin type containing, for example, surfactants, lubricants, and inert fillers such as lactose, sucrose, calcium phosphate, and cornstarch.

In another embodiment, the compounds of this invention may be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quaternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally-occurring phosphatide such as lecithin, a condensation product of an alkylene oxide with a fatty acid, for example, polyoxyethylene stearate, a condensation product of ethylene oxide with a long chain aliphatic alcohol, for example, heptadecaethyleneoxycetanol, a condensation product of ethylene oxide with a partial ester derived from a fatty acid and a hexitol such as polyoxyethylene sorbitol monooleate, or a condensation product of an ethylene oxide with a partial ester derived from a fatty acid and a hexitol anhydride, for example, polyoxyethylene sorbitan monooleate.

The suspensions may also contain one or more preservatives, for example, ethyl or n-propyl p-hydroxybenzoate; one or more coloring agents; one or more flavoring agents; and one or more sweetening agents such as sucrose or saccharin.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin or cetyl alcohol. The sterile injectable preparation may also be a sterile injectable solution or suspension in a non-toxic parenterally-acceptable diluent or solvent. Diluents and solvents that may be employed are, for example, water, Ringer's solution, and isotonic sodium chloride solution. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are, for example, cocoa butter and polyethylene glycol.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring, and coloring agents described above, may also be present.

The compounds of this invention may be formulated as solutions, suspensions, emulsions, powders, and semisolid preparations administered as an aerosol preparation by means of a pressurized aerosol container together with a gaseous or liquefied propellant such as, for example, dichlorodifluoromethane, dichlorodifluoromethane with dichlorodifluoroethane, carbon dioxide, nitrogen, propane, or the like, with the usual adjuvants such as co-solvents and wetting agents, as may be necessary or desirable. The compounds may also be administered in a non-pressurized form such as in a nebulizer or atomizer. The aerosols are intended for administration as fine, solid particles or as liquid mists via the respiratory system, and the particle size of aerosol preparations intended for administration to the lungs should be below 50 micrometers, in most instances.

The pharmaceutical compositions of the invention may also be in the form of oil-in-water emulsions. The oily phase may be a vegetable oil such as liquid paraffin or a mixture of vegetable oils. Suitable emulsifying agents may be (1) naturally-occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents such as, for example, glycerol, propylene glycol, sorbitol or sucrose. Such formulations may also contain a demulcent, and preservative and flavoring and coloring agents.

The compositions of the invention can also contain other conventional pharmaceutically-acceptable compounding ingredients, generally referred to as carriers or diluents, as necessary or desired. Any of the compositions of this invention may be preserved by the addition of an antioxidant such as ascorbic acid or by other suitable preservatives. Conventional procedures for preparing such compositions in appropriate dosage forms can be utilized.

The following specific examples are presented to illustrate compositions of this invention, but they should not be construed as limiting the scope of this invention in any way.

EXAMPLE 11

A tablet is prepared from:

| | |
|---|---|
| 1,5-dihydro-1,3-diphenyl-4-(N-methylhydroxylamino)-2H-pyrrol-2-one | 250 mg |
| Starch | 40 mg |
| Talc | 10 mg |
| Magnesium | 10 mg |

EXAMPLE 12

A capsule is prepared from:

| | |
|---|---|
| 3-(4-benzyloxyphenyl)-1,5-dihydro-4-(N-methylhydroxylamino)-1-(4-pyridyl)-2H-pyrrol-2-one | 400 mg |
| Talc | 40 mg |
| Sodium Carboxymethyl cellulose | 40 mg |
| Starch | 120 mg |

The compounds of this invention may also be utilized in research and diagnostics, or as analytical references or standards, and the like. Therefore, the present invention includes general compositions which are comprised of an inert carrier and an effective amount of a compound of Formula I, or a salt thereof. An inert carrier is any material which does not interreact with the compound to be carried and which lends support, means of conveyance, bulk, traceable material, and the like to the compound to be carried. An effective amount of compound is that amount which produces a result or exerts an influence on this particular procedure being performed.

It should be apparent to one of ordinary skill in the art that changes and modifications can be made to this invention without departing from the spirit or scope of the invention as it is set forth herein.

What is claimed is:

1. A compound of the formula:

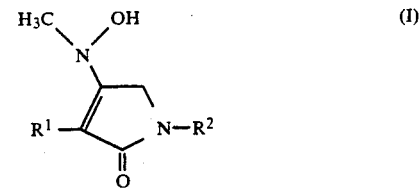

wherein $R^1$ is dibenzofuranyl; and $R^2$ is selected from the group consisting of methyl, 3- or 4-pyridyl and phenyl where the phenyl group is optionally substituted at the 4 position with a methylthio or methylsulfinyl group, or a pharmaceutically acceptable salt thereof.

2. A compound according to claim 1 wherein $R^2$ is methyl, 3- or 4-pyridyl or 4-(methylsulfinyl)phenyl.

3. A compound according to claim 1 which is 3-(2-dibenzofuranyl)-1,5-dihydro-4-(N-methylhydroxylamino)-1-phenyl-2H-pyrrol-2-one.

4. A compound according to claim 1 which is 3-(2-dibenzofuranyl)-1,5-dihydro-4-(N-methylhydroxylamino)-1-(3-pyridyl)-2H-pyrrol-2-one; 3-(2-dibenzofuranyl)-1,5-dihydro-4-(N-methylhydroxylamino)-1-(4-pyridyl)-2H-pyrrol-2-one; 3-(2-dibenzofuranyl)-1,5-dihydro-4-(N-methylhydroxylamino)-1-(4-methylsulfinylphenyl)-2H-pyrrol-2-one.

5. A method of treating the leukotriene mediated conditions of asthma or arthritis which comprises administering a compound of claim 1 to a patient in need thereof, in an amount necessary to effect a result.

6. A method according to claim 1 which comprises a method of treating asthma.

7. A method according to claim 1 which comprises a method of treating arthritis.

8. A pharmaceutical composition comprising an effective amount of a compound of claim 1 or a salt thereof in combination with a pharmaceutically-acceptable carrier.

9. A composition comprising an effective amount of a compound of claim 1 or a salt thereof, in combination with an inert carrier.

* * * * *